US006528038B1

(12) United States Patent
Reynolds et al.

(10) Patent No.: US 6,528,038 B1
(45) Date of Patent: Mar. 4, 2003

(54) PORPHYROMONAS GINGIVALIS ANTIGENS FOR THE DIAGNOSIS AND TREATMENT OF PERIODONTITIS

(75) Inventors: Eric Charles Reynolds, North Balwyn (AU); Nada Slakeski, Kew (AU); Anne Hendtlass, Balwyn (AU)

(73) Assignee: The University of Melbourne, Victoria (AU)

(*) Notice: Subject to any disclaimer, the term of this patent is extended or adjusted under 35 U.S.C. 154(b) by 0 days.

(21) Appl. No.: 09/101,307

(22) PCT Filed: Apr. 1, 1997

(86) PCT No.: PCT/AU97/00212
§ 371 (c)(1),
(2), (4) Date: Jul. 7, 1998

(87) PCT Pub. No.: WO97/36923
PCT Pub. Date: Oct. 9, 1997

(30) Foreign Application Priority Data

Mar. 29, 1996 (AU) ............................................. PN 9012

(51) Int. Cl.⁷ ..................... A61K 49/00; A61K 39/00; A61K 39/02
(52) U.S. Cl. ................. 424/9.2; 424/184.1; 424/190.1; 424/234.1; 514/900; 514/901; 514/902; 530/300; 530/350; 536/23.1; 536/23.7
(58) Field of Search ............................... 424/9.2, 184.1, 424/190.1, 234.1; 514/900, 901, 902; 530/300, 350; 536/23.1, 23.7

(56) References Cited

U.S. PATENT DOCUMENTS 5,523,390 A    6/1996    Travis et al. ............... 536/23.2

FOREIGN PATENT DOCUMENTS

| AU | B 21148/92 | 4/1993 | ......... G01N/33/569 |
| WO | 96/17936 | 6/1996 | ........... C12N/15/31 |

*Primary Examiner*—Rodney P Swartz
(74) *Attorney, Agent, or Firm*—Nixon & Vanderhye

(57) ABSTRACT

The present invention provides a composition for use in raising an immune response directed against *Porphyromonas gingivalis*. The composition includes a suitable adjuvant and/or acceptable carrier and one substantially purified *P. gingivalis* immunogen. The immunogen is selected from the group consisting of Antigen 1, Antigen 2, Antigen 3, Antigen 4 and epitope containing fragments thereof, in which: Antigen 1 is an antigen of *P. gingivalis* and has an internal amino acid sequence: DLENKGEATLLVTFGSSYKAPRETYAKIEKTFAAAYPDQR; Antigen 2 is an antigen of *P. gingivalis* and has an internal amino acid sequence: DNPDENPLEGDITQTHTEKYVLAED; Antigen 3 is an antigen of *P. gingivalis* and has an internal amino acid sequence: DVLLLDVTPLSLGIETMGGVMTYLIDANTTIPKLK; Antigen 4 is an antigen of *P. gingivalis* and has an internal amino acid sequence: VYNASISAVGNTSAIDPVVQIIHHN.

8 Claims, 2 Drawing Sheets

```
     TTGCGACTCGCCACATCGCATCGTTTCGCTCATTTCCGCCACATCATCCTGGATGGAACG
   1 ------------------------------------------------------------
     CTCGGTATAGACAACCGTTTGACTACGTGGATGATCGTCCTATGGGTGTCAATTATGCTA
  61 ------------------------------------------------------------
     CCGTAACGCCGGGACGTACTTTCTTTGCTCAAATAGCGATTCGATTCAACAACTAATGTC
 121 ------------------------------------------------------------
     TCACAAATTAATTTAAGAACAGAGATGAAAAAACTGATTTTAGCGACTTTGGGACTTATG
 181 ------------------------------------------------------------+
                         M  K  K  L  I  L  A  T  L  G  L  M
     GCCATTGCCATGCTCTCATGTTCAAGCAACAACAAGGATTTGGAGAACAAAGGGCAGGCT
 241 ------------------------------------------------------------
      A  I  A  M  L  S  C  S  S  N  N  K  D  L  E  N  K  G  E  A
     ACTCTTTTGGTAACGTTTGGTAGCTCCTATAAAGCTCCACGCGAAACCTATGCGAAGATT
 301 ------------------------------------------------------------
      T  L  L  V  T  F  G  S  S  Y  K  A  P  R  E  T  Y  A  K  I
     GAGAAGACTTTTGCCGCAGCTTATCCCGATCAAAGGATAAGCTGGACATACACGTCTTCT
 361 ------------------------------------------------------------
      E  K  T  F  A  A  A  Y  P  D  Q  R  I  S  W  T  Y  T  S  S
     ATTATCCGAAAGAAACTGGCTCAGCAGGGTATTTATATCGATGCTCCGGATGAGGCTTTG
 421 ------------------------------------------------------------
      I  I  R  K  K  L  A  Q  Q  G  I  Y  I  D  A  P  D  E  A  L
     GAGAAATTGGCTCGTCTGGGTTATAAGAAGATCAATGTACAGAGTCTTCATGTGATTCCC
 481 ------------------------------------------------------------
      E  K  L  A  R  L  G  Y  K  K  I  N  V  Q  S  L  H  V  I  P
     GGCCGAGAATATGATGAGATGATCGACTTTGTCAATAAGTTTAAGGCAGCACATAGTGAT
 541 ------------------------------------------------------------
      G  R  E  Y  D  E  M  I  D  F  V  N  K  F  K  A  A  H  S  D
     ATTACTGTGAAGGTAGGGCGTCCGCTTTTCGATACCGATGAAGATATGCGCGAGGTGGCA
 601 ------------------------------------------------------------
      I  T  V  K  V  G  R  P  L  F  D  T  D  E  D  M  R  E  V  A
     GAGATCTTGCACAAGCGTTTTCAGCAAACGATAGAGAAAGGTGAAGCTATTGTATTCATG
 661 ------------------------------------------------------------
      E  I  L  H  K  R  F  Q  Q  T  I  E  K  G  E  A  I  V  F  M
     GGACACGGCACCGAGCATGCTGCCAATGACAGGTATGCCCGTATCAATAAGATCATGAAG
 721 ------------------------------------------------------------
      G  H  G  T  E  H  A  A  N  D  R  Y  A  R  I  N  K  I  M  K
     AACTATAGCAAGTTCATGATCGTCGGAACCGTCGAGTCCGATCCCTCTATCAATGATGTT
 781 ------------------------------------------------------------
      N  Y  S  K  F  M  I  V  G  T  V  E  S  D  P  S  I  N  D  V
     ATTGCCGAACTGAAAGAAACCGGTGCCACGGCCGTAACAATGATGCCGCTGATGAGTGTG
 841 ------------------------------------------------------------
      I  A  E  L  K  E  T  G  A  T  A  V  T  M  M  P  L  M  S  V
     GCAGGCGACCATGCTACGAATGATATGGCCGGAGATGAGGACGATAGCTGGAAGACGTTG
 901 ------------------------------------------------------------
      A  G  D  H  A  T  N  D  M  A  G  D  E  D  D  S  W  K  T  L
     CTGACCAATGCCGGCTACACAGTTTCTATAGACAAGCTGGACAATGCAATTTCTCAGCT
 961 ------------------------------------------------------------
      L  T  N  A  G  Y  T  V  S  I  D  K  L  D  N  G  N  F  S  A
     CTTGGAGATATAGAAGAGATCCGGAATATCTGGCTCAAGCATATGAAAGCCACCTCTGCT
1021 ------------------------------------------------------------
      L  G  D  I  E  E  I  R  N  I  W  L  K  H  M  K  A  T  S  A
     CGCTAAGGACGGGCGGATATGCAATGAGACAATCAAGCAATTAAGTTACGAGAGCACTTA
1081 ------------------------------------------------------------+
      R  *
```

```
     TTGCGACTCGCCACATCGCATCGTTTCGCTCATTTCCGCCACATCATCCTGGATGGAACG
   1 ------------------------------------------------------------
     CTCGGTATAGACAACCGTTTGACTACGTGGATGATCGTCCTATGGGTGTCAATTATGCTA
  61 ------------------------------------------------------------
     CCGTAACGCCGGGACGTACTTTCTTTGCTCAAATAGCGATTCGATTCAACAACTAATGTC
 121 ------------------------------------------------------------
     TCACAAATTAATTTAAGAACAGAGATGAAAAAACTGATTTTAGCGACTTTGGGACTTATG
 181 ------------------------------------------------------------
                                  M  K  K  L  I  L  A  T  L  G  L  M

GCCATTGCCATGCTCTCATGTTCAAGCAACAACAAGGATTTGGAGAACAAAGGGGAGGCT
 241 ------------------------------------------------------------
      A  I  A  M  L  S  C  S  S  N  N  K  D  L  E  N  K  G  E  A

ACTCTTTTGGTAACGTTTGGTAGCTCCTATAAAGCTCCACGCGAAACCTATGCAAGATT
 301 ------------------------------------------------------------
      T  L  L  V  T  F  G  S  S  Y  K  A  P  R  E  T  Y  A  K  I

GAGAAGACTTTTGCCGCAGCTTATCCCGATCAAAGGATAAGCTGGACATACACGTCTTCT
 361 ------------------------------------------------------------
      E  K  T  F  A  A  A  Y  P  D  Q  R  I  S  W  T  Y  T  S  S

ATTATCCGAAAGAAACTGGCTCAGCAGGGTATTTATATCGATGCTCCGGATGAGGCTTTG
 421 ------------------------------------------------------------
      I  I  R  K  K  L  A  Q  Q  G  I  Y  I  D  A  P  D  E  A  L

GAGAAATTGGCTCGTCTGGGTTATAAGAAGATCAATGTACAGAGTCTTCATGTGATTCCC
 481 ------------------------------------------------------------
      E  K  L  A  R  L  G  Y  K  K  I  N  V  Q  S  L  H  V  I  P

GGCCGAGAATATGATGAGATGATCGACTTTGTCAATAAGTTTAAGGCAGCACATAGTGAT
 541 ------------------------------------------------------------
      G  R  E  Y  D  E  M  I  D  F  V  N  K  F  K  A  A  H  S  D

ATTACTGTGAAGGTAGGGCGTCCGCTTTTCGATACCGATGAAGATATGCGCGAGGTGGCA
 601 ------------------------------------------------------------
      I  T  V  K  V  G  R  P  L  F  D  T  D  E  D  M  R  E  V  A

GAGATCTTGCACAAGCGTTTTCAGCAAACGATAGAGAAGGTGAAGCTATTGTATTCATG
 661 ------------------------------------------------------------
      E  I  L  H  K  R  F  Q  Q  T  I  E  K  G  E  A  I  V  F  M

GGACACGGCACCGAGCATGCTGCCAATGACAGGTATGCCCGTATCAATAAGATCATGAAG
 721 ------------------------------------------------------------
      G  H  G  T  E  H  A  A  N  D  R  Y  A  R  I  N  K  I  M  K

AACTATAGCAAGTTCATGATCGTCGGAACCGTCGAGTCCGATCCCTCTATCAATGATGTT
 781 ------------------------------------------------------------
      N  Y  S  K  F  M  I  V  G  T  V  E  S  D  P  S  I  N  D  V

ATTGCCGAACTGAAAGAAACCGGTGCCACGGCCGTAACAATGATGCCGCTGATGAGTGTG
 841 ------------------------------------------------------------
      I  A  E  L  K  E  T  G  A  T  A  V  T  M  M  P  L  M  S  V

GCAGGCGACCATGCTACGAATGATATGGCCGGAGATGAGGACGATAGCTGGAAGACGTTG
 901 ------------------------------------------------------------
      A  G  D  H  A  T  N  D  M  A  G  D  E  D  D  S  W  K  T  L

CTGACCAATGCCGGCTACACAGTTTCTATAGACAAGCTGGACAATGGCAATTTCTCAGCT
 961 ------------------------------------------------------------
      L  T  N  A  G  Y  T  V  S  I  D  K  L  D  N  G  N  F  S  A

CTTGGAGATATAGAAGAGATCCGGAATATCTGGCTCAAGCATATGAAAGCCACCTCTGCT
1021 ------------------------------------------------------------
      L  G  D  I  E  E  I  R  N  I  W  L  K  H  M  K  A  T  S  A

CGCTAAGGACGGGCGGATATGCAATGAGACAATCAAGCAATTAAGTTACGAGAGCACTTA
1081 ------------------------------------------------------------
      R  *
```

Figure 1

PORPHYROMONAS GINGIVALIS ANTIGENS FOR THE DIAGNOSIS AND TREATMENT OF PERIODONTITIS

FIELD OF THE INVENTION

This invention relates to oral compositions and immunogenic compositions for use in the suppression of the pathogenic effects of the bacterium *Porphyromonas gingivalis* associated with periodontal disease and cardiovascular disease. It also relates to diagnostic tests for the presence of *Porphyromonas gingivalis* in subgingival plaque samples and specific antibodies against *P. gingivalis* antigens. The compositions comprise proteins, peptides or oligopeptides or peptide chimeras of specific antigens of *Porphyromonas gingivalis*. Also disclosed are methods for preparing the antigens, peptide components and peptide chimeras using recombinant DNA and/or biochemical techniques. Related thereto, disclosed are the DNA sequences encoding the specific antigens, and recombinant vectors useful in directing the expression of antigen constructs containing major epitopes. Also disclosed are host cells transformed with such recombinant vectors. The proteins, peptides, oligopeptides and peptide chimeras are useful as immunogens in formulations for use in raising an immune response and can be used to generate protein-specific and peptide-specific antisera useful for passive immunization and as reagents for diagnostic assays. The nucleotide sequences disclosed provide for the synthesis of corresponding oligonucleotides which can be used as reagents in diagnostic assays directed to the detection of *P. gingivalis* genetic material and incorporated into expression vectors for use as genetic vaccine formulations.

BACKGROUND OF THE INVENTION

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is *Porphyromonas gingivalis* as the recovery of this microorganism from adult periodontitis lesions can be up to 50% of the subgingival anaerobically cultivable flora, whereas *P. gingivalis* is rarely recovered, and then in low numbers, from healthy sites. A proportional increase in the level of *P. gingivalis* in subgingival plaque has been associated with an increased severity of periodontitis and eradication of the microorganism from the cultivable subgingival microbial population is accompanied by resolution of the disease. The progression of periodontitis lesions in non-human primates has been demonstrated with the subgingival implantation of *P. gingivalis*. These findings in both animals and humans suggest a major role for *P. gingivalis* in the development of adult periodontitis. The presence of *P. gingivalis* in atheromatous plaques has also been associated with the development of cardiovascular disease.

*P. gingivalis* is a black-pigmented, anaerobic, proteolytic Gram-negative rod that obtains energy from the metabolism of specific amino acids. The microorganisms has an absolute growth requirement for iron, preferentially in the form of heme or its Fe(III) oxidation product hemin and when grown under conditions of excess hemin is highly virulent in experimental animals. A number of virulence factors have been implicated in the pathogenicity of *P. gingivalis* including the capsule, adhesins, cytotoxins and extracellular hydrolytic enzymes. In order to develop an efficacious and safe vaccine to prevent *P. gingivalis* colonisation it is necessary to identify protein antigens that are involved in virulence that have utility as immunogens to generate neutralising antibodies.

SUMMARY OF THE INVENTION

The present inventors purified and characterised four major *P. gingivalis* antigens using serum from a healthy subject that harboured *P. gingivalis* in subgingival plaque as shown by DNA probe analysis. The antigens (Ag1, Ag2, Ag3 and Ag4) are listed below.

| A | $M_r$ | Putative Function | Internal Amino acid sequence |
|---|---|---|---|
| Ag1 | 32 kDa | Haeme receptor | DLENKGEATLLVTFGSSYKAPRETYAKIEK TFAAAYPDQR (SEQ ID NO: 1) |
| Ag2 | 46 kDa | Fimbrial protein | DNPDENPLEGDITQTHTEKYVLAED (SEQ ID NO: 2) |
| Ag3 | 70 kDa | DnaK homologue | DVLLLDVTPLSLGIETMGGVMTYLIDANTT IPKLK (SEQ ID NO: 3) |
| Ag4 | 10 kDa | S-layer protein | VYNASISAVGNTSAIDPVVQIIHHN (SEQ ID NO: 4) (N-terminal sequence) |

Accordingly in a first aspect the present invention consists in a composition for use in raising an immune response directed against *Porphyromonas gingivalis*, the composition including a suitable adjuvant and/or acceptable carrier and one substantially purified *P. gingivalis* immunogen, the immunogen being selected from the group consisting of Antigen 1, Antigen 2, Antigen 3, Antigen 4 and epitope containing fragments thereof. Optionally, the composition may further include at least one additional purified *P. gingivalis* immunogen, the immunogen being selected from the group consisting of Antigen 1, Antigen 2, Antigen 3, Antigen 4 and epitope containing fragments thereof.

In a second aspect, the present invention consists in a substantially purified *P. gingivalis* antigen or epitope containing fragment thereof, wherein antigen has an internal amino acid sequence:
DLENKGEATLLVTFGSSYKAPRETYAK-IEKTFAAAYPDQR (SEQ ID NO:1). It is preferred that the antigen has an amino acid sequence as shown in FIG. 1 (SEQ ID NOS:5 and 6).

In a third aspect, the present invention consists in a substantially purified *P. gingivalis* antigen or epitope containing fragment thereof, wherein antigen has an internal amino acid sequence:

DNPDENPLEGDITQTHTEKYVLAED (SEQ ID NO:2).

In a fourth aspect, the present invention consists in a substantially purified P. gingivalis antigen or epitope containing fragment thereof, wherein antigen has an internal amino acid sequence:

DVLLLDVTPLSLGIETMGGVMTYLIDANTTIPKLK (SEQ ID NO:3). It is preferred that the antigen includes an amino acid sequence encoded by the open reading frame of the clone deposited with AGAL under accession No. NM 97/04974 which hybridises with degenerate probes corresponding to the amino acid sequence DVLLLDVTPLSLGI-ETMGGVMTYLIDANTTIPKLK (SEQ ID NO:3).

In a fourth aspect, the present invention consists in a substantially purified P. gingivalis antigen antigen or epitope containing fragment thereof, wherein antigen has an internal amino acid sequence: VYNASISAVGNTSAIDPVVQII-HHN (SEQ ID NO:4).

In other aspects, the present invention consists in nucleotide sequences encoding Ag1, Ag2, Ag3 and Ag4 and probes which hybridise to these sequences.

The nucleotide sequence encoding Ag1 and deduced amino acid sequence of the haeme receptor protein Ag1 is shown in FIG. 1. The disclosure of the nucleotide sequence includes within its scope degeneracy equivalents and subsequences coding for amino acid sequences corresponding to antigenic determinants of P. gingivalis W50.

A clone containing nucleotide sequence from Ag3, DnaK clone #6, has been deposited under the terms of the Budapest Treaty with Australian Government Analytical Laboratories, 1 Suakin Street, Pymble, NSW Australia on Mar. 25, 1997 and has been accorded accession No. NM 97/04974. Accordingly further nucleotide sequence for this antigen can be obtained by accessing this deposit. Access to this deposit is available under the terms and conditions of the Budapest Treaty. Where applicable access to this deposit is to be limited to independent experts (EPC Rule 28(4). AU Reg. 3.25(3)).

In another aspect the present invention consists in antibodies raised against the antigens of the present invention.

Antibodies against the antigens can be used in oral compositions such as toothpaste and mouthwash to neutralise the antigens and thus prevent disease. Antigen-specific antibodies can also be used for the early detection of P. gingivalis in subgingival plaque samples by a diagnostic assay. A vaccine based on these antigens and suitable adjuvant delivered by nasal spray, orally or by injection to produce a specific immune response against these antigens thereby reducing colonisation and virulence of P. gingivalis and thereby preventing or reducing disease. The antigen proteins and antigen peptides (herein termed "peptides") and antigen oligopeptides (herein termed "oligopeptides") and antigen chimeric peptides containing epitopes of one antigen fused with the epitopes of another (herein termed "chimeric peptides") thereof, of the present invention may be used as immunogens in prophylactic and/or therapeutic vaccine formulations; or as an antigen in diagnostic immunoassays directed to detection of P. gingivalis infection by measuring an increase in serum titer of P. gingivalis—specific antibody. Also antigen protein, peptides, oligopeptides and chimeric peptides of the present invention may be used to generate antigen-specific antibody which may be useful for passive immunotherapy and as reagents for diagnostic assays directed to detecting the presence of P. gingivalis in clinical specimens such as subgingival plaque samples. Peptides, oligopeptides or chimeric peptides can be obtained by chemical synthesis, purification from P. gingivalis cultures, or produced from recombinant vector expression systems using the nucleic acid sequences disclosed herein.

Accordingly, in other aspects the invention provides oral compositions including toothpastes and mouthwashes which include antibodies raised against any one or a combination of antigens Ag1, Ag2, Ag3 and Ag4.

In another aspect the invention provides a method of early detection of P. gingivalis comprising a diagnostic assay involving the use of antibodies raised against any one or a combination of antigens Ag1, Ag2, Ag3 and Ag4.

In another aspect, the invention provides a method for the detection of P. gingivalis infection comprising the measure of an increase in serum titer to any one of the P. gingivalis antigens as herein described.

Other aspects of the present invention are directed to the construction of novel DNA sequences involving antigen constructs and vectors including plasmid DNA, and viral DNA such as human viruses, animal viruses, insect viruses, or bacteriophages which can be used to direct the expression of antigen protein, peptides, oligopeptides or chimeric peptides in appropriate host cells from which the expressed protein or peptides may be purified.

Another aspect of the present invention provides methods for molecular cloning of the genes encoding the antigens Ag1, Ag2, Ag3 and Ag4, and gene fragments encoding antigen peptides or oligopeptides or chimeric peptides.

The nucleic acid sequences of the present invention can be used in molecular diagnostic assays for P. gingivalis genetic material through nucleic acid hybridization, and including the synthesis of antigen sequence-specific oligonucleotides for use as primers and/or probes in amplifying, and detecting amplified, nucleic acids. Additionally, antigen protein, peptides, oligopeptides, chimeric peptides and antigenic constructs containing epitopes can be used as immunogens in prophylactic and/or therapeutic vaccine formulations against pathogenic strains of P. gingivalis, whether the immunogen is chemically synthesized, purified from P. gingivalis, or purified from a recombinant expression vector system. Alternatively, the genes encoding the antigens, or one or more gene fragments encoding peptides or oligopeptides or chimeric peptides, may be incorporated into a bacterial or viral vaccine comprising recombinant bacteria or virus which is engineered to produce one or more immunogenic epitopes of each antigen by itself, or in combination with immunogenic epitopes of other antigens or from other pathogenic microorganisms. In addition, the genes encoding the antigens or one or more gene fragments encoding peptides or oligopeptides or chimeric peptides, operatively linked to one or more regulatory elements, can be introduced directly into humans to express protein, peptide, oligopeptides or chimeric peptides relating to the antigens to elicit a protective immune response. A vaccine can also be based upon a recombinant component of a mutated antigen incorporated into an appropriate vector and expressed in a suitable transformed host (e.g. E. coli, Bacillus subtilis, Saccharomyces cerevisiae, COS cells, CHO cells and HeLa cells) containing the vector. The vaccine can be based on an intra-oral recombinant bacterial vaccine, where the recombinant bacterium expressing antigen is a commensal inhabitant of the oral cavity. Unlike whole P. gingivalis cells or other previously prepared antigens, the four antigens described herein are safe and effective antigens for the preparation of a vaccine for the prevention of P. gingivalis-associated periodontal disease.

In yet another aspect the present consists in a composition for use in raising an immune response directed against *Porphyromonas gingivalis*, the composition including a suitable adjuvant and/or acceptable carrier and a DNA molecule including a sequence encoding one *P. gingivalis* immunogen, the immunogen being selected from the group consisting of Antigen 1, Antigen 2, Antigen 3, Antigen 4 and epitope containing fragments thereof. *P. gingivalis* has an absolute growth requirement for Fe which it prefers in the form of haeme. As such, Ag1 is of particular interest as neutralisation of this haeme receptor by specific antibodies would prevent haeme uptake and therefore growth and virulence. *P. gingivalis* grown haeme-limited is less virulent in animal models.

Fimbriae are thin, filamentous structures that either completely cover the cell or are polar. There are at least two fimbrial types recognized: those involved in the transfer of genetic material by the formation of conjugation bridges, and those involved in adherence to soft and hard tissues. The fimbriae involved in conjugation are referred to as sex pili. These pili have specific receptors for attachment to a genetically compatible recipient bacterium. The second fimbrial type, the type specific or common pili are involved in eubacterial coaggregation and adherence to eukaryotic cells and often play an important role in prevention of phagocytosis and the invasion of host tissue. In the Enterobacteriaceae, the fimbriae consist of repeating subunit proteins of approximately 17 to 21 kDa. Minor proteins are also part of the fimbriae structure. The specific fimbrial binding proteins (adhesins) are often 28 to 31 kDa and located at the tip or periodically along the length of the fimbriae.

Yoshimura et al. were amongst the first to demonstrate the presence of fimbriae on *P. gingivalis* and they purified a 43 kDa fimbrilin subunit which has no amino acid sequence homology with fimbrilins from other Gram-negative bacteria. Genco and coworkers have shown that the 43 kDa fimbrial protein and synthetic peptides corresponding to the C-terminal end of the fimbrilin reduced adherence of *P. gingivalis* 381 to saliva-coated hydroxyapatite. In a subsequent study they showed that a recombinant fimbrilin binds specifically to statherin and proline-rich proteins of saliva. Immunisation of rats with the 43 kDa protein protected against periodontal tissue destruction induced by infection with *P. gingivalis* 381. Further, an isogenic mutant of *P. gingivalis* 381 with the fimA gene, that encodes the 43 kDa fimbrilin, insertionally inactivated was significantly less able to produce periodontal tissue destruction in the rat model when compared with the wild-type strain. In this study it should be noted however, that the fimA mutant still did produce greater periodontal tissue destruction than occurred in the sham infected animals. The fimA mutant was unimpaired in its ability to agglutinate red blood cells, coaggregate with other oral bacteria although binding to saliva-coated hydroxyapatite was reduced. In an independent study Hamada et al. also produced a fimA mutant of *P. gingivalis* ATCC 33277 by homologous recombination of an insertionally inactivated gene and noted that although the mutant failed to express long (0.5 to 1.0 μm) fimbriae, thin, short fimbrial structures could still be observed by electron microscopy suggesting the presence of a second fimbrial type. The identification of the 43 kDa fimbrilin and the virulence and immunisation studies related to the 43 kDa protein have been conducted with the *P. gingivalis* strains 381 and ATCC 33277. These strains are classified as non-invasive and are considered to be less virulent than invasive strains based on the infective process in animal models. Non-invasive strains produce a localised abscess at the challenged site, whereas invasive strains at the same inoculum spread to distant sites and produce multiple abscesses. Further, Sundqvist et al. showed that the non-invasive strains (381 and ATCC 33277) were phagocytosed and killed by polymorphonuclear leukocytes to a high extent whereas the invasive strains W50 and W83 were poorly phagocytosed and killed. It is interesting to note that Naito et al. suggest that there is a difference in the fimbriae of invasive and non-invasive *P. gingivalis* strains. These workers found that the fimbriae of non-invasive strains bound to collagen-coated hydroxyapatite (HA) in high numbers whereas the fimbriae prepared from invasive strains bound to collagen-coated HA weakly. The *P. gingivalis* invasive strains W50, W83 and AJW5 are highly virulent in animal models but do no express the 43 kDa fimbrilin as shown by immunocytochemistry and Western blot analysis. However, on fine negative staining, W50 and W83 are fimbriated although less densely than other strains. It appears that W50 and W83 possess inactive fimA genes accounting for the lack of the 43 kDa fimbrilin however these strains are still virulent and invasive despite lacking the 43 kDa fimbrilin.

Ag2 is the second fimbrial type or a major adhesin of *P. gingivalis*. As part of a study to purify and characterise cell surface protein antigens of *P. gingivalis* W50 we purified a 30 kDa fragment of the 46 kDa fimbrial protein (Ag2) that was seroreactive with serum from a healthy subject that harboured *P. gingivalis* subgingivally as shown by DNA probe analysis. The internal amino acid sequence of the 30 kDa fragment showed considerable homology (48% identity) to a fimbrial protein of Dichelobacter (formerly Bacteroides) nodosus.

*P. gingivalis* 30 kDa fragment DNPDENPLEGDITQTH-TEKYVLAED (SEQ ID NO:2) . . . *D. nodosus* fimbrial protein KGPDANPASGVVGNKDTGKYVLAEI . . . (SEQ ID NO:7)

The *D. nodosus* fimbrial protein is classified as a type-IV or mePhe pilin which is a common fimbrial type of a group of Gram-negative bacteria including Bacteroides spp., *Neisseria gonorrhoeae, Neisseria meningitidis, Acinetobacter calcoaceticus, Eikenella corrodens, Moraxella bovis, Moraxella nonliquefaciens* and several species of Pseudomonas including *P. aeruginosa* (Elleman, 1988). The *P. gingivalis* 30 kDa fragment exhibits the highest homology with the conserved amino acyl residues of the central domain of the *D. nodosus* A-set or Class I fimbriae (including the serotypes A, B, C, E, F, and G). A characteristic of the type-TV fimbriae is that they adhere to eukaryotic cells and agglutinate red blood cells. It is interesting to note that the conserved hexapeptide motif-KYVLAE- (SEQ ID NO:8) which is also present in the *P. gingivalis* 46 kDa fimbrial protein has been localised to, or near to, the receptor binding site of gonococcal pili since antisera to these residues prevents bacterial attachment to eukaryotic cells even by heterologous pili and precipitates larger peptide fragments which bind to eukaryotic cells. It has been suggested that the conserved residues of the central domain when juxtaposed form a cleft which specifically interacts with the carbohydrate moieties of surface glycoproteins of eukaryotic cells.

*D. nodosus* is the aetiological agent of the contagious disease of sheep, interdigital dermatitis or footrot, and the type-IV fimbriae are the major serological and immunoprotective virulence factors. Footrot vaccines have evolved from simple bacterins to highly specific recombinant DNA fimbrial vaccines. The initial whole cell vaccines were unsuccessful due to the short duration of immunity and incorporation of limited serotypes. A number of antigens were examined and the major protective immunogen was the type-IV fimbrial subunit protein. Monovalent vaccines based on recombinant fimbriae are omnipotent inducing long lasting immunity. The homology between the *P. gingivalis* 46 kDa fimbrial protein and the *D. nodosus* immunoprotective fimbriae indicate that the *P. gingivalis* protein (Ag2) would have application in diagnostic and immunoprophylactic products for *P. gingivalis*-related periodontitis.

The heat shock or stress response of cells is a homeostatic mechanism that enables cells to survive environmental stresses such as temperature elevation that can result in denaturation of cellular proteins. The DnaK family of proteins bind to denatured and incorrectly folded proteins and facilitate refolding to the original conformation and function. The DnaK or Heat Shock Protein (HSP) 70 is a highly conserved molecular chaperonin common to bacterial and eukaryotic cells comprising 1–5% of the constitutive cellular protein, with 15% of DnaK in *E. coli* being associated with vesicles. During stress DnaK can be overexpressed to constitute up to 30% of total cellular protein making this protein an ideal candidate for a sensitive immunodiagnostic test. Specific diagnostic tests for leprosy and tuberculosis have been developed based on the respective DnaK protein homologues. All species homologues of DnaK are highly conserved in the N-terminal half of the protein with the species-specific regions of the molecule in the C-terminal half. The *P. gingivalis* DnaK homolgue (Ag3) therefore would have application in diagnostic and immunoprophylactic products for *P. gingivalis*-related periodontitis.

The four antigens identified (Ag1, Ag2, Ag3 and Ag4) are of particular interest for diagnostics and neutralisation by passive immunity through oral compositions containing neutralising antibodies and by vaccine development. In particular for the development of an intra-oral recombinant bacterial vaccine, where the recombinant bacterium expressing the antigens is a genetically engineered commensal inhabitant of the oral cavity. The superiority of these four antigens to prior disclosed *P. gingivalis* antigens, is that these are major virulence-associated factors and contain conserved epitopes on invasive strains making them ideal for the development of diagnostic and immunoprophylactic products.

DETAILED DESCRIPTION OF THE INVENTION

The present invention will now be described in detail with reference to the following particularly preferred embodiments which are not limiting to the invention but representative of the methods of performing certain aspects of the invention.

The four antigens Ag1, Ag2, Ag3 and Ag4 can be purified from *P. gingivalis* cells by chloroform extraction followed by anion exchange, gel filtration and reversed-phase chromatography. The purified antigens are then used to generate polyclonal or monoclonal antibodies using standard techniques. The animals used for antibody generation can be mice, rabbits, goats, chickens, sheep, horses, cows etc. When a high antibody titre against the antigens is detected by immunoassay the animals are bled or eggs or milk are collected and the serum prepared and/or antibody purified using standard techniques or monoclonal antibodies produced by fusing spleen cells with myeloma cells using standard techniques. The antibody (immunoglobulin fraction) may be separated from the culture or ascites fluid, serum, milk or egg by salting out, gel filtration, ion exchange and/or affinity chromatography, and the like, with salting out being preferred. In the salting out method the antiserum or the milk is saturated with ammonium sulphate to produce a precipitate, followed by dialyzing the precipitate against physiological saline to obtain the purified immunoglobulin fraction with the specific antibody. The preferred antibody is obtained from the equine antiserum and the bovine antiserum and milk. In this invention the antibody contained in the antiserum and milk obtained by immunising the animal with the antigens is blended into the oral composition. In this case the antiserum and milk as well as the antibody separated and purified from the antiserum and milk may be used. Each of these materials may be used alone or in combination of two or more. Antibodies can be used in oral compositions such as toothpaste and mouthwash to neutralise *P. gingivalis* and thus prevent disease. The antibodies can also be used for the early detection of *P. gingivalis* in subgingival plaque samples by a chairside Enzyme Linked Immunosorbent Assay (ELISA).

For oral compositions it is preferred that the amount of the above antibodies administered is 0.0001–50 g/kg/day and that the content of the above antibodies is 0.0002–10% by weight preferably 0.002–5% by weight of the composition. The oral composition of this invention which contains the above-mentioned serum or milk antibody may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. The oral composition according to this invention may further include additional well known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred. The pH of such liquid and other preparations of the invention is generally in the range of from about 4.5 to about 9 and typically from about 5.5 to 8. The pH is preferably in the range of from about 6 to about 8.0, preferably 7.4. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50.000 cm$^2$/gm., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal alumino-silicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4$^{th}$ Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP).

There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10–30% by weight. Other polishing materials are typically present in amount of about 30–75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5–30% w/w of water, 0 to about 70% w/w of glycerine and about 20–80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% SiO$_2$, 25.40% MgO, 3.05% Na$_2$O, 0.98% Li$_2$O, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244).

Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable.

The organic surface-active material is preferably anionic, nonionic or ampholytic in nature which does not denature the antibody of the invention, and it is preferred to employ as the surface-active agent a detersive material which imparts to the composition detersive and foaming properties while not denaturing the antibody. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material.

The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use with antibodies are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1–5% by weight. It is noteworthy, that the surface active agent may assist in the dissolving of the antibody of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavor and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or such as glucose, sorbitol and the like.

Another important form of the invention is a composition for use in raising an immune response directed against *P. gingivalis* based on the four antigens and suitable adjuvant and/or carrier. This may be delivered via a number of routes, for example by nasal spray, orally or by injection to produce a specific immune response against the antigen thereby reducing colonisation of *P. gingivalis* and reducing virulence thereby preventing disease. As will be readily understood the composition may be based upon a recombinant antigen incorporated into an appropriate vector and expressed in a suitable transformed host (e.g. *E. coli, Bacillus subtilis, Saccharomyces cerevisiae,* COS cells, CHO cells and HeLa cells) containing the vector. Unlike whole *P. gingivalis* cells or other previously prepared antigens, the antigens described herein or peptides, oligopeptides or chimeric peptides are safe and effective antigens for the preparation of a vaccine for the prevention of *P. gingivalis*-associated periodontal disease. The antigenic protein, peptides, oligopeptides and chimeric peptides of the present invention, can be produced using recombinant DNA methods as illustrated herein, or can be synthesized chemically from the amino acid sequence disclosed in the present invention. Additionally, peptides can be produced from enzymatic or chemical cleavage of the purified antigens. Antigenic protein, peptides, and oligopeptides with immunogenic epitopes combined, can be used as immunogens in various vaccine formulations in the prevention of periodontal diseases. Additionally, according to the present invention, antigenic protein and related peptides or chimeras produced may be used to generate *P. gingivalis* antisera useful for passive immunization against periodontal disease and infections caused by *P. gingivalis*.

As opposed to use of the antigens themselves in eliciting an immune response this may be achieved by administration of a DNA molecule including a sequence encoding at one of the antigens or epitope containing fragment(s).

The present invention further provides the nucleotide sequence of the genes encoding the antigens, as well as the amino acid sequence deduced from the isolated genes. According to one particularly preferred embodiment of the present invention, using recombinant DNA techniques the genes encoding the antigens or gene fragments encoding one or more peptides or chimeras having immunogenic epitopes, is incorporated into an expression vector, and the recombinant vector is introduced into an appropriate host cell thereby directing the expression of these sequences in that particular host cell. The expression system, comprising the recombinant vector introduced into the host cell, can be used (a) to produce antigenic protein, related peptides, oligopeptides or chimeras which can be purified for use as an immunogen in vaccine formulations; (b) to produce antigenic protein, related peptides, oligopeptides and chimeras to be used as an antigen for diagnostic immunoassays or for generating *P. gingivalis*-specific antisera of therapeutic and/or diagnostic value; (c) or if the recombinant expression vector is a live virus such as vaccinia virus, the vector itself may be used as a live or inactivated vaccine preparation to be introduced into the host's cells for expression of antigen or immunogenic peptides or oligopeptides or chimeric peptides; (d) for introduction into live attenuated bacterial cells or genetically engineered commensal intra-oral bacteria which are used to express antigenic protein, related peptides or oligopeptides or chimeras to vaccinate individuals; (e) or for introduction directly into an individual to immunize against the encoded and expressed antigenic protein, related peptides, or oligopeptides or chimeras. In particular the recombinant bacterial vaccine can be based on a commensal inhabitant of the human oral cavity or animal if the vaccine is to prevent periodontal disease in animals. The recombinant bacterial vaccine expressing antigen can be used to colonise the oral cavity, supragingival or subgingival plaque. The intra-oral bacterium can be isolated from the patient with periodontitis and genetically engineered to express the antigen, peptides or chimeras. The production of the *P. gingivalis* antigen within the oral cavity will not be toxic to the oral mucosal tissues. However, the expressed antigen will stimulate the mucosal-associated lymphoid tissues (MALT) to produce specific antibody to neuralise and reduce the virulence of *P. gingivalis*.

BRIEF DESCRIPTION OF THE DRAWINGS

The invention will now be described in further detail with reference to the accompanying drawings, in which:

FIG. 1 is the nucleotide sequence and deduced amino acid sequence of Ag1 (SEQ ID NOS:5 and 6)

EXAMPLES

Figure 2:
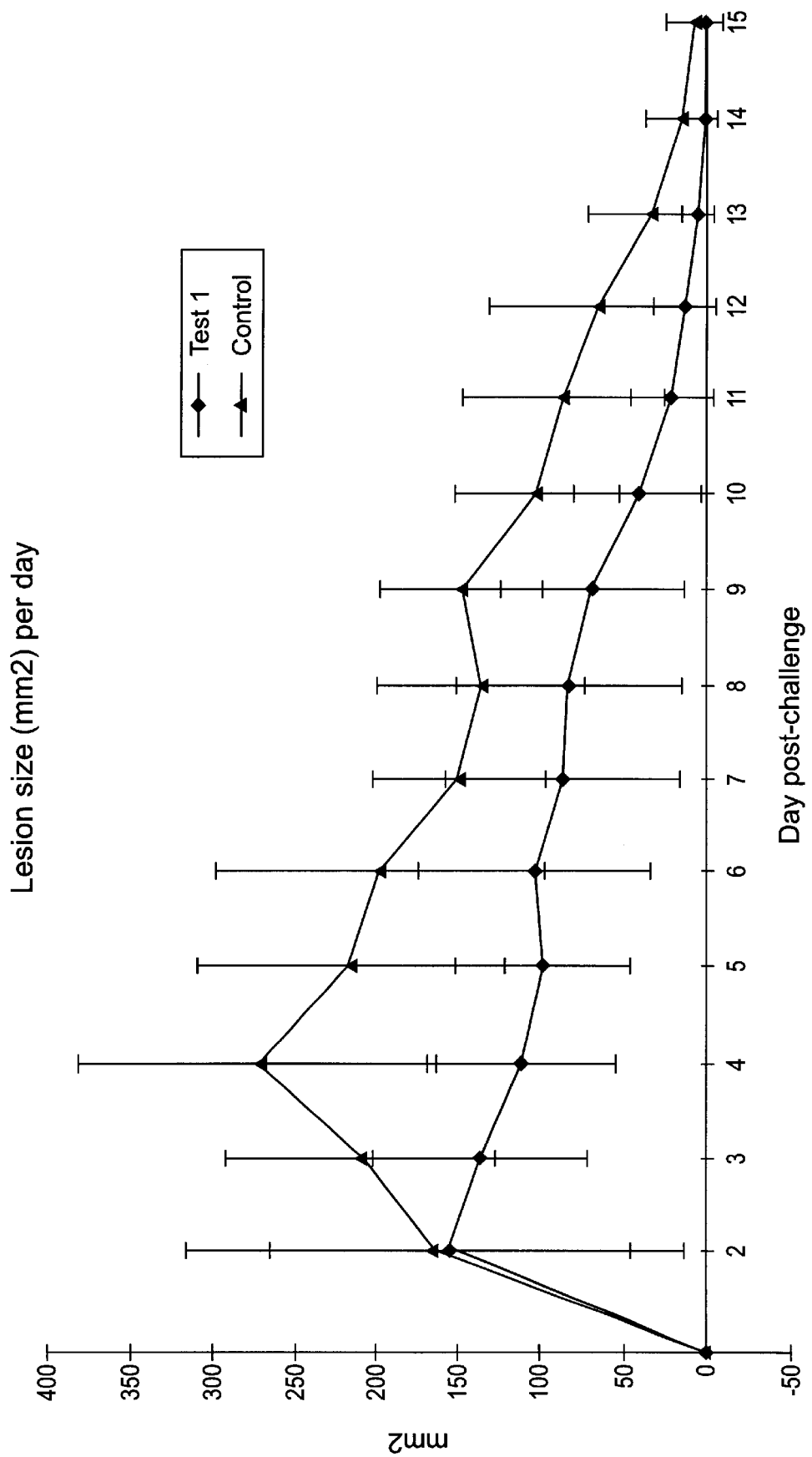
FIG. 2 is a plot of lesion size for mice collected day by day following challenge.

The following examples are further illustrative of the nature of the present invention, but it is understood that the invention is not limited thereto. All amounts and proportions referred to herein and in the appended claims are by weight unless otherwise indicated.

Example 1

Preparation of Antigen 1

Extraction and Purification of Ag1

*P. gingivalis* cells were harvested at $O.D._{650nm}$ 0.18 by centrifugation at 5,000×g for 20 min at 4° C. The cell pellet was incubated with 10 ml chloroform per L of original cell culture with gentle rocking at room temperature for 15 min together with 50 ml Buffer A (50 mM NaCl, 10 mM Tris, 10 mM EDTA, pH 8.0) per litre of original culture. The sample was centrifuged at 6,000×g for 20 min to separate the phases. The aqueous phase was removed and centrifuged a further 30 min at 10,000×g to eliminate contaminating cell debris. The supernatant was passed through a 0.22 μm filter before being applied to a Q sepharose anion exchange chromatography column (XK16/10) at 4° C. using an FPLC™ System, (Pharmacia). Proteins were eluted from the column using a linear NaCl gradient from 50 mM NaCl to 500 mM NaCl in 10 mM Tris, 10 mM EDTA, pH 8.0 at 2 ml/min over 180 min. Elution was monitored at 280 nm. Six mL fractions were collected and these were analysed by SDS-PAGE and ELISA using a healthy subject's serum to assess their antigenicity. The most antigenic fraction was concentrated to 200 μl using a 10,000 NMWCO centricon concentrator before being applied to a Superose 12 (Pharmacia) size-exclusion column.

The size exclusion column was equilibrated and separation was performed in 150 mM NaCl, 20 mM Tris, 10 mM EDTA, pH 8.0 at 0.3 mL/min. Protein standards were run to enable size comparison with resulting sample peaks. Elution was monitored at 280 nm. Five hundred μl fractions were collected and these were analysed by SDS-PAGE and ELISA. A peak eluting at 60 kDa was found to be antigenic with serum from a subject harbouring *P. gingivalis* but showing no signs of periodontitis. This fraction was further purified by reversed-phase chromatography.

Reverse-phase chromatography (RP-HPLC) was performed using a $C_8$RP300 column (Applied Biosystems) and a linear gradient of 0%–80% acetonitrile in 0.1% TFA over 40 min. A single peak eluted which contained a single band on SDS-PAGE analysis that had an Mr of 28 kDa. This peak was characterised by N-terminal sequence analysis using a Hewlett Packard 1005A automated protein sequencer.

From sequence analysis this antigen is likely to be a Haeme receptor of *P. gingivalis* and has an N-terminal amino acid sequence:

DLENKGEATLLVTFGSSYKAPRETYAK-IEKTFAAAYPDQR (SEQ ID NO:1);

SDS-PAGE Analysis

SDS-PAGE analysis was performed using a discontinuous system with a 12% separating gel and a 4% stacking gel. Sample buffer included 4% SDS, and 70 mM β-Mercaptoethanol. Protein standards (Pharmacia) were included on each gel for size comparison. The samples were run at constant voltage of 160 volts in running buffer until the dye-front was near the bottom of the stacking gel. The proteins were visualised with coomassie brilliant blue R-250m, and destained in 40% MeOH. 7% HAC in water.

Western Blot analysis

Western blots were performed to identify proteins which were recognised by serum antibodies from a periodontally diseased (D50) and healthy (H10) subject who harboured *P. gingivalis* subgingivally as shown by DNA analysis. Proteins to be blotted were separated according to the SDS-PAGE procedure above, except that pre-stained standards (BioRad) were included to enable the determination of completion of transfer. Following SDS-PAGE, the gel apparatus was dismantled and the gel, PVDF membrane (ProBlott, Applied Biosystems), blotting paper and fibre pads were equilibrated in transfer buffer (10% CAPS, 10% MeOH) for 5 mins. The proteins within the SDS-PAGE gel were transferred onto the PVDF membrane at a constant voltage of 60 volts for 90 min. After transfer the PVDF membrane was blocked with 5% skim milk powder at room temperature for 1 hr. The membrane was then incubated with the primary antibody (human serum H10 1/10 or D50 1/50 diluted in TN buffer (25 mM Tris, 0.5 M NaCl, pH 7.5)) at 4° C. overnight. The membrane was washed 3 times for 10 min each in TN buffer then incubated with the second antibody (Horseradish peroxidase conjugated goat anti-human IgG, 1/1000 diluted in TN buffer) at room temperature for 2 hours. Once again the membrane was washed 3 times in TN buffer for 10 min each. Binding of the goat anti-human IgG to the antigenic proteins was visualised with 6 mg 4-chloro-1-napthol, 2 mL MeOH, 10 mL TN buffer and 6 μl $H_2O_2$. The enzyme reaction was stopped with water.

The Western blot analysis showed that the 28 kDa antigen was recognised by the healthy subject (H10) but not by the patient suffering from periodontitis (D50).

ELISA

ELISAs were performed using the serum antibodies from a periodontally diseased (D50) and healthy (H10) subject who harboured *P. gingivalis* subgingivally as shown by DNA analysis. Microtitre plates were coated with the 28 kDa protein or 2% w/v skim milk powder as a negative control, diluted in 50 mM Tris, 200 mM NaCl, pH 7.4 (TBS). The plates were blocked by adding TBS containing 0.05% w/v Tween-20 (TBST) and 2% w/v skim milk powder. The wells were washed three times with TBST then incubated with human serum diluted 1/500 in TBST containing 2% w/v polyvinyl-pyrrolidone-40 and 1% w/v NGS (Antibody Diluting Buffer, ADB) for 2 hours at room temperature. The wells were washed three times with TBST then incubated with goat anti-human IgG-horseradish peroxidase diluted 1/3000 in ADB for 2 hours at room temperature. Binding of the anti-human Ig-HRP to the *P. gingivalis* cell-surface proteins was visualised with 10 mg/mL 3,3',4,4' tetramethylbenzidine dissolved in dimethyl sulphoxide diluted 1:100 with 0.1 M sodium acetate/citric acid buffer pH 6.0 and 0.004% w/v $H_2O_2$. The enzyme reaction was stopped with 2 M $H_2SO_4$ and the colour intensity of the reaction product was spectrophotometrically quantitated by measurement of absorbance at 450 nm.

The ELISA confirmed that the 28 kDa antigen was recognised by the healthy subject (H10) harbouring *P. gingivalis* but not by the patient suffering from periodontitis (D50).

Example 2

Cloning and sequence analysis of the Ag1 gene

A lambda GEM 12 library of BamHI digested *P. gingivalis* genomic DNA was screened using degenerate oligonucleotide probes derived from the N-terminal sequence of the 28 kDa antigen (Ag1). A probe-positive clone was identified and contained an insert of 4.6 kbp of *P. gingivalis* genomic DNA. This insert was purified by phenol extraction and was subcloned into pUC18. The DNA sequence of the gene revealed that the open reading frame encoded a protein of predicted mas 32,709. The sequence was determined using the Sanger dideoxy method and the nucleotide sequence and deduced amino acid sequence of Ag1 is presented in FIG. 1. The deduced amino acid sequence gives a protein of 32,709 in molecular mass.

Example 3

Construction of a DNA Vaccine Using the Ag1 Gene

The plasmid containing the 4.6 kbp of *P. gingivalis* DNA was used as the template for amplification of the gene encoding the 32 kDa antigen (Ag1) by PCR. PCR was performed using the specific oligonucleotide primers with sequences as follows:

N-terminal

Oligo A 5'CAA GCA ACA ACA AGG ATT TGC 3' (SEQ ID NO:9)

C-terminal

Oligo B 5'TTG CAT ATC CGC CCG TCC 3' (SEQ ID NO:10)

The PCR mixture contained: Template DNA 100 ng, $MgCl_2$:1 mM, Oligo A:800 ng, Oligo B:800 ng, 250 mM dNTP, 3U Ultma polymerase (Perkin Elmer). The thermal cycle involved: Denaturation: 94° C., 30 s, Annealing: 52° C., 30 s, and Extension: 70° C., 60 s.

Southern blot analysis using specific oligonucleotide probes confirmed the correct amplicon. This band was purified from a 1.0% agarose gel by phenol extraction. The amplified fragment was blunt-end ligated with Sma1 into pUC18 and sequence analysis confirmed the presence of the gene (Ag1) encoding the full length sequence of antigen 1. The gene was then subcloned into pcDNA3 (Invitrogen). The clone contained the full length Ag1 gene (949 base pairs). Approximately 2 μg of purified pcDNA3 (Invitrogen) plasmid and DNA from the pUC18 clone 2.2 was digested with HindIII (Promega) and EcoRI (Promega) restriction enzymes in Multicore buffer (Promega) at 37° C. for 1 hour. Digested plasmid DNA was run on 1% Nusieve low melting agarose and the *P. gingivalis* insert DNA cut from the gel and purified using a Bresaclean kit (Bresatech) according to the manufacturer's instructions. The purified insert DNA was resuspended in 20 μl of TE buffer. The purified insert DNA from the pUC clones was ligated into the cut pcDNA vector by conventional techniques using T4 ligase (Promega) and ligated at room temperature for 2 hours. Ligated pcDNA3 was transformed into Top10F' *E. coli* cells (Invitrogen) which were plated onto agar plates containing ampicillin. Resultant clones were expanded into 3 ml cultures, plasmids were purified and screened for insertion of the appropriate sized fragment by restriction enzyme digestion and electrophoresis on 1% agarose gels.

Clones showing the correct insert size were selected and further restriction enzymes digests prepared to confirm the insert was correct. This consisted of digesting the clones with the restriction enzymes HindIII alone, HindIII and EcoRI together and NdeI alone. One clone was selected 5.1 containing the full length Ag1 gene. The clone was confirmed by partial DNA sequence analysis using the Sp6 and T7 universal primers following conventional techniques. The identify of the pcDNA3-Ag1 construct in clone 5.1 was confirmed by DNA sequence analysis of the 5' and 3' termini, which were as follows:

N-terminus

5'GCT CCC GGC ATC CGC TTA CAG ACA AGC TGT GAC GTC TCC GGG AGC TGC ATG TGT CAG AGG TTT TCA CCG TCA CCG AAA CGC GCG AGG CTG ATC GTC AGT CAG TCA CGA TGC GGC CGT TCG AGT CGA CTC TAG AGG ATC CCC CAA GCA ACA ACA AGG ATT TGG AGA ACA AAG GGG AGG CTA CTC TTT TGG TAA CGT TTG GTA GCT CCT ATA AAG CTC CA 3' (SEQ ID NO:11)

C-terminus

5'GAT GTG TCA AAG ATA TCT GTT CGA CCT GTT ACC GTT AAA GAG TCG AGA ACC TCT ATA TCT TCT CTA GGC CTT ATA GAC CGA GTT CGT ATA CTT TCG GTG GAG ACG AGC GAT TCC TGC CCG CCT ATA CGT TCC CAT GGC TCG AGC TTA AGG ACC CCT AGG TGC GCT TGG TCT AGG CTA AAA CCT CCT ACC AGC GGT GGT GGT TTG CAC GAA 3' (SEQ ID NO:12)

Bolded bases=insert

Non-bolded bases=vector

Large scale (1L) preparations of plasmid DNA was prepared from the clone 5.1 and also from the pcDNA3 without any insert. Qiagen Mega Preps were used to purify the plasmid DNA from overnight cultures of Top 10F' *E. coli* cells grown in Terrific broth with 150 μg/ml of ampicillin. Purified plasmid DNA was checked by restriction enzyme analysis to confirm the insert size and the purity of the DNA. The concentration of DNA/RNA was calculated spectrophotometrically by determining the absorption at 280 nm/260 nm.

Purified plasmid DNA from the pcDNA3-Ag1 clone with insert (5.1) and pcDNA3 (no insert) was diluted into 0.9% NaCl in sterile water to 0.5 mg/ml of DNA for injection into animals.

Example 4

The Ability of the Ag1 DNA Vaccine Construct to Protect Against *P. gingivalis* Challenge in the Murine Lesion Model 10 mice received the pcDNA3-Ag1 construct containing the Ag1 gene described above (test group), an other 10 mice received pcDNA3 vector (control group). 25 μg of DNA was injected into each tibialis muscle (a total of 50 μg DNA/mouse) of the 20 female, 6 weeks old, Balb/c mice. This was followed a month later with boosts of 25 μg of DNA into each tibialis muscle. The mice were subcutaneously challenged on the back with $3.4 \times 10^9$ cfu *P. gingivalis* W50 approximately 3.5 cm from the base of the tail.

Each day for 14 days the mice were monitored for weight loss, lesion size and behaviour. At the end of this period the mice were sacrificed as was any mouse with a weight loss greater or equal to 20% during the 14 days. At sacrifice serum was prepared from blood collected by cardiac puncture. Lesion size data for each mouse was collected each day for 14 days and are presented in FIG. 2. The lesion sizes for the two groups of animals (test and control) were analysed by ANOVA (single factor) and Mann-Whitney non-parametric statistical tests. This showed that the difference in lesion size between the test and the control groups was significant (p=0.027 and p=0.019) using both tests examined. These results showed that the DNA vaccine construct containing the Ag1 gene protected mice against challenge with *P. gingivalis* W50.

Example 5

Immunogenicity of a Synthetic Peptide Corresponding to the C-terminal Region of Antigen 1

The following synthetic peptide, CIRNIWLKHMKAT-SAR (SEQ ID NO:13) corresponding to the C-terminal region of Ag1 was prepared based on the presence of a predicted B-cell epitope. Polyclonal antisera were raised in two dutch rabbits and one New Zealand white rabbit by immunisation with the 16mer peptide conjugated to diptheria toxoid.

The rabbits were immunised with 78 μg of peptide dissolved in TBS (50 mM Tris, 200 mM NaCl, pH 7.4) and emulsified with an equal volume of Freunds incomplete adjuvant. The preparation was injected subcutaneously in four locations on the back. Four weeks later this was repeated and after 2 weeks a test bleed was performed and the serum response observed by ELISA against a biotinylated form of the peptide. After 2 weeks the rabbits were immunised again using the same procedures. Two weeks following the final immunisation the rabbits were bled by cardiac puncture and the serum response determined by ELISA and western blot. ELISA was performed using the polyclonal antisera against the biotinylated 16 mer. Microtitre plates were coated with 2.54 µg/mL streptavidin. The wells were washed three times with TBS (50 mM Tris HCl pH 7.4, 200 mM NaCl) and incubated with 0.2 µg/mL biotin conjugated peptide diluted in TBS overnight at 4° C. The following day the wells were washed three times with TBS containing 0.05% v/v Tween20 (TBST) and blocked for 1 hour with 2% w/v skim milk powder at room temperature. The wells were washed three times with TBST and incubated with the polyclonal antiserum at 5-fold dilutions from 1/100 in Antibody Diluting Buffer (ADB)[TBST containing 2% w/v skim milk powder] for 2 hours at room temperature. The wells were washed three times with TBST and incubated with horseradish peroxidase conjugated goat anti-rabbit IgG diluted 1/3000 in ADB for 2 hours at room temperature. The wells were washed three times with TBST and binding of the antiserum to *P. gingivalis* proteins was visualised as above. A specific response was demonstrated indicating that specific and anti-peptide antibodies had been generated. An ELISA performed using *P. gingivalis* cell-surface proteins also produced a specific response indicating that the peptide had generated antibodies capable of recognising the cell surface antigen 1 of *P. gingivalis*.

A western blot was performed to identify the components of the *P. gingivalis* cell-surface extract that was recognised by the anti-peptide antibody. After SDS-PAGE of the *P. gingivalis* cell-surface extract, the proteins were transferred to PVDF membrane and blocked as already described. The membrane was incubated with a 1/100 dilution of the antiserum in TN buffer overnight at 4° C. The following day, the membrane was washed three times in TN buffer and incubated with horseradish peroxidase conjugated goat anti-rabbit IgG diluted 1/1000 in TN buffer for 2 hours at room temperature. The membrane was washed three times in TN buffer and the binding of the serum antibodies to components of the *P. gingivalis* cell-surface protein extract was visualised as descried above. A ladder of bands of 30, 33.9, 37, 40.1, 45.9, 48.8, 51.8, 56.8 and 60.3 kDa was obtained.

These results indicate that the anti-peptide antibody specifically recognised Antigen 1 of *P. gingivalis* and showed that the antigen exists on the surface of *P. gingivalis* i multiple forms possibly associated with LPS.

Example 6

Preparation of Antigens 2, 3 and 4 (Ag2, Ag3 and Ag4)

*P. gingivalis* W50 was grown anaerobically at 37° C. on lysed horse blood agar and in modified BM media containing 1 µg/ml hemin. Bacteria were maintained on lysed horse blood plates by routine passage (<10 passages) and used to inoculate batch cultures. Batch culture growth in Brain Heart Infusion medium was monitored at 650 nm using a spectrophotometer (295E, Perkin-Elmer). Culture purity was checked routinely by Gram stain, microscopic examination and by using a variety of biochemical tests. Stocks were maintained as lyophilised cultures. A culture of *P. gingivalis* was grown to late logarithmic phase and the cells harvested by centrifugation (5,000×g, 20 min, 4° C.). Chloroform was added to the cell pellet and after gentle mixing the suspension was left for 15 min at room temperature. Following chloroform treatment, TMC buffer [20 mM Tris-HCl pH 8.0, 50 mM 2-mercaptoethanol and 5 mM $CaCl_2$] containing 50 mM NaCl was added and gently mixed. This mixture was then centrifuged (100,000×g, 30 min, 4° C.) and the supernatant filtered (0.22 µm) prior to anion-exchange FPLC. The chloroform extract was applied to an anion-exchange column (Hiload XK 16/10 Q Sepharose, Pharmacia-LKB) cooled to 4° C., in multiple injections using a 50 ml superloop (Pharmacia-LKB). The sample was eluted using a linear gradient from 0–100% buffer B over 90 min. The eluant was monitored at 280 nm and collected. Buffer A was TMC containing 50 mM NaCl and buffer B was TMC buffer containing 500 mM NaCl. Anion-exchange fractions were washed and then concentrated in TMC buffer containing 150 mM NaCl. The fractions were then applied to a gel filtration (Superose 12) column using TMC buffer containing 150 mM NaCl. The eluant was monitored at 280 nm and peaks collected. The $M_r$ values of eluant peaks were determined using high and low molecular mass gel filtration standards (Pharmacia-LKB). Collected peaks were then subjected to reversed-phase (RP) HPLC using a $C_8$ RP-300 Brownlee column eluting with an acetonitrile gradient. The protein concentration of fractions and purified samples was determined using the Bradford protein assay (Biorad) with BSA as a standard. Chromatographic fractions and purified proteins were analysed by SDS-PAGE and Western blotting using sera from subjects with *P. gingivalis* subgingivally as shown by DNA probe analysis. Serum H10 was from a subject harbouring *P. gingivalis* subgingivally but displaying no clinical signs of periodontal disease. Serum D50 was from a patient with periodontitis who harboured *P. gingivalis* in subgingival plaque samples. From a combination of ELISA and Western blot analyses of chromatographic fractions from the anion exchange, gel filtration and reversed-phase HPLC, three purified antigens, that were recognised by the H10 serum but were only weakly or not at all recognised by the D50 serum, were identified. The first antigen was a 30 kDa protein with an N-terminal amino acid sequence:

DNPDENPLEGDITQTHTEKYVLAED (SEQ ID NO:2)

This antigen is a fragment of a larger protein (vide infra) that has a molecular weight of about 46 kDa, and from sequence homology is a putative fimbrial subunit protein or adhesion of *P. gingivalis*.

The second antigen was a 30 kDa protein with an N-terminal amino acid sequence:

DVLLLDVTPLSLGIETMGGVMTYLIDANTTIPKLK (SEQ ID NO:3)

This antigen, from sequence homology, is a C-terminal fragment of the *P. gingivalis* 70 kDa DnaK homologue.

The third antigen recognised by the H10 serum had a molecular weight of about 10 kDa and an N-terminal amino acid sequence:

VYNASISAVGNTSAIDPVVQIIHHN (SEQ ID NO:4).

From sequence homology it is proposed that this protein is an S-layer protein of *P. gingivalis*.

Example 7

Cloning and Sequence Analysis of the Gene Encoding Ag3 (DnaK) of *Porphyromonas gingivalis*

A partial BamH1 *P. gingivalis* genomic library (W50 strain), constructed into bacteriophage vector LambdaGEM- 12 was screened with a mixture of oligonucleotides derived from the amino acyl sequences of Ag3. The genomic library was screened by in situ hybridization with a mixture of degenerate oligonucleotides made to the segment of the purified protein sequence of Ag3 the 70 kDa DnaK homologue GIETMGG (SEQ ID NO:14).

Hybridisation was carried out overnight at 39° C. in 6 X SSC. 5 X Denhardt's solution. 50 µg herring sperm DNA, 1% SDS, pH 7.0. Filters were washed in 2 X SSC. 0.1% SDS at 39° C. and exposed to Amersham X-ray Hyperfilm overnight at −80° C. Bacteriophage DNA was prepared from single positive phage clones by the plate lysate method (See Amersham's cDNA Cloning System-λgt protocols booklet). Positively hybridizing restriction fragments were subcloned into the plasmid pUC18. Double stranded plasmid DNA was then used as sequencing template using the dideoxy-chain termination method (kits obtained from Bresatec and USB).

A clones containing the nucleotide sequences encoding Ag3 (DnaK clone #6) has been isolated and deposited with the Australian Government Analytical Laboratory with accession number NM/04974.

Example 8

The Immunogenicity of a Synthetic Peptide Corresponding to an Internal Sequence of Antigen 2 (Fimbrial Peptide)

The peptide H-DNPDENPLEGDITQTHTEKYVLAEDC-NH$_2$ (DNP-EDC) (SEQ ID NO:15) from Antigen2 (fimbrial protein) from *Porphyromonas gingivalis* strain W50 was synthesised and coupled to tetanus toxoid (TT) using 6-maleimidocaproic acyl N-hydroxysuccinimide ester forming a thioether bond. White Dutch rabbits were inoculated subcutaneously at 4 sites with 100 mg of peptide coupled to the protein carrier, emulsified with incomplete Freunds adjuvant. Rabbits were inoculated with a second dose on day 35 after the first injection. Rabbits were bled from the marginal ear vein on day 10 and day 84 from the first inoculation. Collected rabbit antisera was then used for ELISA and western blot analysis.

Detection of fimbrial peptide specific antibodies by Enzyme-Linked ImmunoSorbent Assay (ELISA).

Fimbrial peptide solution (50 µl at 5 µg ml$^{-1}$ of peptide) in TBS was used to coat wells of flat-bottomed polyvinyl microtiter plates (Microtiter, Dynatech Laboratories, VA., U.S.A.) overnight at room temperature in a humidified atmosphere. After removal of the coating solution, a solution (250 µl) of 1% gelatin in TBS containing 0.05% Tween 20 (TBST) was added to block the remaining uncoated plastic. After 1.5 h at 37° C. the plates were washed four times with TBST. A 1 in 100 dilution of the relevant antibodies in TBS containing 0.5% gelatin were prepared and serially diluted across the plate and incubated for 3 hours at 37° C. in a humidified atmosphere. Plates were washed six times (TBST) and 50 µl of a 1/4000 dilution of horse radish peroxidase (HRPO) goat immunoglobulin (Ig) directed against rabbit Ig (BioRad, USA). After 1.5 hours at 37° C., free antibody-HRPO conjugate was removed by washing the plates six times (TBST). Bound antibody was detected by the addition of 100 µl of substrate (0.1 M acetate buffer pH 6 containing 0.01% of a 49 mM tetramethyl benzidine in DMSO and 0.004% H$_2$O$_2$. The colour reaction was stopped by the addition of 2 M H$_2$SO$_4$. Optical density (O.D.) at 455 nm was measured using a BioRad plate reader (BioRad. USA).

The binding of antisera raised against DNP–EDC-conjugate to plate bound DNP–EDC peptide was assessed. Pre-immune serum did not bind to the fimbrial peptide, however antisera from rabbits immunised with DNP–EDC-conjugate induced high titres of anti-peptide antibody. This indicates that within the peptide sequence DNP–EDC one or more B-cell epitopes are present.

Western blot analysis of *P. gingivalis* strain W50 cell sonicate probed with anti-DNP–EDC (fimbrial peptide) antibodies.

A SDS-Polyacrylamide gel containing low molecular weight standards (Amrad-Pharmacia, Australia), low molecular weight prestained standards (BioRad. USA) and *Porphyromonas gingivalis* W50 cell sonicate (20 µg) was prepared and transfered onto ProBlott (ABI, USA) using the following technique. ProBlott was wetted with methanol for a few seconds and placed in a tray containing the electroblotting buffer (10 mM 3-[cyclohexylamino]-1-propanesulfonic acid containing 10% methanol, pH 11). The SDS-Polyacrylamide gel of *Porphyromonas gingivalis* W50 cell sonicate was also soaked in electroblotting buffer for 5 minutes. The transblotting sandwich was assembled and electroblotted at a constant voltage of 60 volts for 90 minutes. The ProBlott was removed and rinsed with milli-Q water before staining. The ProBlott was soaked with methanol for a few seconds and the standards were stained with 0.1% Coomassie blue R-250 in 40% aqueous methanol containing 1% acetic acid. The ProBlott was destained with 50% aqueous methanol and rinsed with milli-Q water.

The ProBlott was soaked in 5% (w/v) of non-fat dry milk in 25 mM Tris/HCl in 0.5 M NaCl. pH 7.5 (TN buffer) over night at 4° C. to prevent non-specific binding. The Western blot was incubated at room temperature with a 1/200 dilution of the antisera in TN buffer for 2 hours. The Western blot was then washed 4 times in TN buffer containing 0.1% triton X-100 (TNT buffer) and incubated with a 1/2000 dilution of horseradish peroxidase-conjugated goat anti-rabbit IgG (BioRad. USA) in TN buffer for 1 hour. The Western blot was then washed 4 times with TNT buffer and the protein bands detected with 0.05% 4-chloro-1-napthol in TN buffer 16.5% ice cold methanol and 0.05% H$_2$O$_2$. Colour development was stopped with de-ionised water and the Western blot air-dried between two filter papers.

Intact fimbrial protein (adhesin) from *P. gingivalis* was detected by immunostaining using antisera raised against the fimbrial peptide-conjugate. Only two bands were detected with molecular weights of 41 and 46 kDa. This suggests that the intact fimbrial protein (adhesin) of *P. gingivalis* W50 has a molecular weight of 46 kDa and the 41 kDa band is a truncated form of the 46 kDa protein.

Example 9

Preparation of Antibodies

Serum antibodies can be obtained by immunising horses, rabbits, sheep or dairy cows with Ag (1–4).

Immunizations are carried out using standard procedures. The initial immunisation is with a mixture of the antigen and Freund's incomplete adjuvant. The antibodies could be recovered from the animals serum or milk using standard procedures.

Example 10

This example illustrates that nucleotide sequences encoding the antigens or portions thereof, can be inserted into, and expressed by various vectors including phage vectors and plasmids. Successful expression of the protein and peptide requires that either the insert comprising the gene or gene fragment, or the vector itself, contain the necessary elements for transcription and translation which is compatible with, and recognized by the particular host system used for expression. DNA encoding the antigen, related peptides, or oligopeptides or chimeric peptides can be synthesized or isolated and sequenced using the methods and sequences as illustrated herein. A variety of host systems may be utilized to express the antigens, related peptides or oligopeptides or chimeras, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccina virus, adenovirus, adeno-associated virus, retrovirus, etc.).

Using methods known in the art of molecular biology, including methods described above, various promoters and enhancers can be incorporated into the vector or the DNA sequence encoding antigen amino acid sequences, related peptides or oligopeptide or chimeras, to increase the expression of the antigen amino acid sequences, provided that the increased expression of the amino acid sequences is compatible with (for example, non-toxic to) the particular host cell system used. Thus and importantly, the DNA sequence can consist of the genes encoding the antigens, or any segment or combined segments of the genes which encode functional epitopes of the proteins. Further, the DNA can be fused to DNA encoding other antigens, such as other bacterial outer membrane proteins, or other bacterial, fungal, parasitic, or viral antigens to create a genetically fused (sharing a common peptide backbone) multivalent antigen for use as an improved vaccine composition. The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription have been observed in a host cell system comprising E. coli include the lac promoter, trp promoter, recA promoter, ribosomal RNA promoter, the $P_R$ and $P_L$ promoters, lacUV5, ompF, bla, lpp, and the like, may be used to provide transcription of the inserted DNA sequence encoding antigen amino acid sequences.

Additional, if antigen, related peptides or oligopeptides or chimeras may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthiobeta-D-galactoside). A variety of operons such as the trp operon, are under different control mechanisms. The trp operon is induced when tryptophan is absent in the growth media. The $P_L$ promoter can be induced by an increase in temperature of host cells containing a temperature sensitive lambda repressor. In this way, greater than 95% of the promoter-directed transcription may be inhibited in uninduced cells. Thus, expression of recombinant antigenic protein, related peptides, or oligopeptides or chimeras may be controlled by culturing transformed or transfected cells under conditions such that the promoter controlling the expression from the inserted DNA encoding antigen amino acid sequences is not induced, and when the cells reach a suitable density in the growth medium, the promoter can be induced for expression from the inserted DNA.

Other control elements for efficient gene transcription or message translation include enchancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted DNA sequences encoding antigenic amino acid sequences to increase transcriptional efficiency. As illustrated previously in this example, other specific regulatory sequences have been identified which may effect the expression from the gene encoding antigen and related peptides or chimera. These or other regulatory sites, such as transcription or translation initiation signals, can be used to regulate the expression of the gene encoding antigen, or gene fragments thereof. Such regulatory elements may be inserted into DNA sequences encoding antigenic amino acid sequences or nearby vector DNA sequences using recombinant DNA methods described herein for insertion of DNA sequences.

Accordingly, P. gingivalis nucleotide sequences containing regions encoding antigen, related peptides, or oligopeptides or chimeras can be ligated into an expression vector at a specific site in relation to the vector's promoter, control, and regulatory elements so that when the recombinant vector is introduced into the host cell the P. gingivalis-specific DNA sequences can be expressed in the host cell. For example, the antigen-specific DNA sequences containing their own regulatory elements can be ligated into an expression vector in a relation or orientation to the vector promoter and control elements which will allow for co-expression of more than one antigen. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid, immunoscreening for production of specific epitopes using antisera generated to the specific antigens, and probing the DNA of the host's cells for antigen-specific nucleotide sequence using one or more oligonucleotides and methods described herein.

Genetic engineering techniques may also be used to characterize, modify and/or adapt the encoded antigenic peptides or protein. For example, site-directed mutagenesis to modify the protein in regions outside the protective domains, may be desirable to increase the safety and solubility of the subfragment to allow for easier purification and safer use. Further, genetic engineering techniques can be used to generate DNA sequences encoding a portion of the amino acid sequence of antigen. Restriction enzyme selection may be done so as not to destroy the immunopotency of the resultant peptide or oligopeptide or chimera. Antigenic sites of a protein may vary in size but can consist of from about 7 to about 14 amino acids. Thus, an antigenic protein will contain many discrete antigenic sites; therefore, many partial gene sequences could encode antigenic epitopes. Thus sequences can be constructed to contain muliple epitopes and used in an expression system to generate highly antigenic chimeric peptides or oligopeptides or proteins. Combination of two or more proteins or peptides may result in increased immunogenicity. When using combinations of antigens these antigens may be related (ie from the same gene sequence or from a closely related gene from the same organism). Alternatively, the antigens may be generated from a related organism (ie another oral bacterium present in subgingival plaque), or from a more distantly-related organism. In particular the host organism for the vector containing the antigen-related genes and constructs can be a commensal inhabitant of the oral cavity: for example an inhabitant of subgingival plaque, supragingival plaque or a bacterium associated with the oral mucosa. Examples of commensal intra-oral bacteria would be Streptococcus species and Actinomyces species, e.g. *Streptococcus salivarius, Streptococcus sanguis, Streptococcus gordonii, Actinomyces naeslundii*. These organisms can be isolated from the periodontitis patient and then genetically engineered to express the *P. gingivalis* antigen, peptides or chimeras. The DNA encoding the antigen, peptides or chimeras could be linked with DNA encoding leader sequences of extracellular proteins of these commensal intra-oral bacteria. The DNA encoding the antigen, peptides or chimeras could also be linked with, or inserted into, the DNA encoding extracellular proteins to produce secreted fusion proteins. Examples of extracellular proteins that could be used to produce fusion proteins with the antigens, peptides or chimeras could be the glucosyltranferases (GTF) or fructosyltransferases (FTF). The recombinant organism would be then re-introduced into the patients oral cavity and once colonised the oral mucosa or teeth would express the *P. gingivalis* antigen, peptide, chimera or fusion to stimulate the muscosal associated lymphoid tissue to produce neutralising antibodies.

The DNA fragment encoding an antigen may be fused to other DNA sequences to allow for improved expression and/or purification procedures (ie DNA sequences cloned into the vector pTrxFus, are expressed as fusions to the *E. coli* protein thioredoxin). This linkage imparts the characteristics of thioredoxin to the fusion protein which offers soluble expression of normally insoluble or difficult to express proteins. After purification, the native protein is released by removal of the entire thioredoxin by digestion with enterokinase). Furthermore, the antigen may be used as a hapten by fusion to other sequences which may increase immunogenicity, if the expressed protein or peptide is not immunogenic. Alternatively, insert DNA sequences cloned into vectors may contain the native promoter sequence of the gene. Therefore, transcription of the protein or peptide of interest is primarily directed from the promoter contained within the insert rather than a promoter contained within the vector sequence itself.

The plasmid expression system described uses the pUC-derived pTrcHis expression vector from Invitrogen. This vector allows high-level expression of DNA sequences by the presence of the Trc promoter (containing the −35 region of the Trp promoter together with the −10 region of the lac promoter) and an rrnB anti-terminator element. The pTrcHis vectors also contain a copy of the lacI$^q$ gene which encodes the lac repressor protein. Therefore, expression of the recombinant protein/peptide is induced by addition of 1mM IPTG (de-repression) to *E. coli* grown to mid-log phase. The DNA fragment is inserted into the multiple cloning site which is positioned downstream and in frame with a sequence that encodes an N-terminal fusion peptide. The N-terminal fusion peptide encodes (from 5' to 3'); an ATG translation initiation codon, a series of 6 histidine residues that function as a metal-binding domain in the translated protein, a transcript stabilising the sequence from gene 10 of phage T7, and an enterokinase cleavage recognition sequence. A DNA fragment encoding a *P. gingivalis* antigen, peptide, oligopeptide or chimera is ligated to the expression vector pTrcHis. The vector was previously treated with calf intestinal phosphatase to prevent reconstitution of non-recombinant vector. The ligation mixture was used to transform *E. coli* strain TOP10 by the heat-shock transformation procedure. Cells harbouring the recombinant vector plasmid were selected on Ampicillin-containing LB medium. Plasmid DNA, purified from Ampicillin-resistant colonies was analysed for the presence of recombinant insert by DNA restriction analysis and hybridisation techniques using antigen-specific oligonucleotides and DNA fragments as probes. The metal-binding domain of the fusion peptide allows for one-step purification of the recombinant proteins by Immobilised Metal Affinity Chromatography. Recombinant antigen in cell culture lysates of cells harbouring the recombinant plasmid is purified by high-affinity binding to ProbondJ resin (Invitrogen). ProbondJ is a nickel-charged sepharose resin that is used to purify recombinant proteins containing a poly-histidine binding domain. Bound proteins are eluted from the ProbondJ resin with either low pH buffer or by competition with imidazole or histidine. The poly-histidine leader peptide may be subsequently removed by digestion of the recombinant expressed protein with Enterokinase. Enterokinase recognises the endopeptidase recognition sequence that is engineered between the poly-His affinity tag and the multiple cloning site in the vector to allow for cleavage of poly-His tail away from the protein of interest. The purified, recombinant antigen may then be used in the generation of antibodies, vaccines and the formulation of diagnostic assays as discussed.

Example 11

Methods for using antigen-specific nucleotide sequences in molecular diagnostic assays for the detection of *P. gingivalis*. Because of the conservation of the genes encoding the antigens described herein, the nucleic acid sequences of the present invention can be used in molecular diagnostic assays for detecting *P. gingivalis* genetic material. In particular, antigen sequence-specific oligonucleotides can be synthesized for use as primers and/or probes in amplifying, and detecting amplified, nucleic acids from *P. gingivalis*. Recent advances in molecular biology have provided several means for enzymatically amplifying nucleic acid sequences. Currently the most commonly used method, PCR™ (polymerase chain reaction Cetus Corporation) involved the use of Taq Polymerase, known sequences as primers, and heating cycles which separate the replicating deoxyribonucleic acid (DNA) strands and exponentially amplify a gene of interest. Other amplification methods currently under development include LCR™ (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA™ (nucleic acid sequence-based amplification, Cangene Corporation) which can be performed on RNA or DNA as the nucleic acid sequence to be amplified.

Nucleic acid probes that are capable of hybridization with specific gene sequences have been used successfully to detect specific pathogens in biological specimens at levels of sensitivity approaching $10^3$–$10^4$ organisms per specimen (1990, *Gene Probes for Bacteria*. Eds. Macario and deMacario, Academic Press). Coupled with a method that allows for amplification of specific target DNA sequences, species-specific nucleic acid probes can greatly increase the level of sensitivity in detecting organisms in a clinical specimen. Use of these probes may allow direct detection without relying on prior culture and/or conventional biochemical identification techniques. This embodiment of the present invention is directed to primers which amplify species-specific sequences of the genes encoding the major antigens of P. gingivalis described herein, and to probes which specifically hybridize with these amplified DNA fragments. By using the nucleic acid sequences of the present invention and according to the methods of the present invention, as few as one P. gingivalis organism may be detected in the presence of 10 ug/ml extraneous DNA.

This embodiment is directed to species-specific oligonucleotides which can be used to amplify sequences of P. gingivalis DNA, if present, from DNA extracted from clinical specimens including subgingival plaque, sputum, blood, abscess and other fluids to subsequently determine if amplification has occurred. In one embodiment of the present invention, a pair of P. gingivalis-specific DNA oligonucleotide primers are used to hybridize to P. gingivalis genomic DNA that may be present in DNA extracted from a clinical specimen, and to amplify the specific segment of genomic DNA between the two flanking primers using enzymatic synthesis and temperature cycling. Each pair of primers are designed to hybridize only to the P. gingivalis nucleotide sequences of the present invention to which they have been synthesized to complement; one to each strand of the double-stranded DNA. Thus, the reaction is specific even in the present of microgram quantities of heterologous DNA. For the purposes of this description, the primer derived from the sequence of the positive (gene) strand of DNA will be referred to as the "positive primer", and the primer derived from the sequence of the negative (complementary) strand will be referred to as the "negative primer".

Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the P. gingivalis DNA sequences, if present, results. Further identification of the amplified DNA fragment, as being derived from P. gingvalis DNA, may be accomplished by liquid hybridization. This test utilizes one or more labelled oligonucleotides as probes to specifically hybridize to the amplified segment of P. gingivalis DNA. Detection of the presence of sequence-specific amplified DNA may be accomplished using any one of several methods known in the art such as a gel retardation assay with autoradiography. Thus, the nucleotide sequences of the present invention provide basis for the synthesis of oligonucleotides which have commercial applications in diagnostic kits for the detection of P. gingivalis. In a related embodiment, the oligonucleotides used as primers may be labeled directly, or synthesized to incorporate label. Depending on the label used, the amplification products can then be detected, after binding onto an affinity matrix, using isotopic or colorimetric detection.

DNA may be extracted from clinical specimens which may contain P. gingivalis using methods known in the art. For example, cells contained in the specimen may be washed in TE buffer and pelleted by centrifugation. The cells then may be resuspended in 100 ul of amplification reaction buffer containing detergents and proteinase K. Using the polymerase chain reaction, the resultant sample may be composed of the cells in 10 mM Tris pH 8.3, 50 mM KCl, 1.5 mM $MgCl_2$, 0.01% gelatin, 0.45% NP40™, 0.045% Tween 20™, and 60 ug/ml proteinase K. The sample is incubated in a 55° C. water bath for 1 hour. Following the incubation, the sample is incubated at 95° C. for 10 minutes to heat-inactivate the proteinase K. The sample may then be amplified in accordance with the protocol for the polymerase chain reaction as set forth below.

The P. gingivalis DNA may be amplified using any one of several protocols for amplifying nucleic acids by the polymerase chain reaction. In one mode of this embodiment, the gene encoding the DnaK may be amplified from clinical isolates of P. gingivalis using the following conditions. DNA to be amplified (1 μg of genomic DNA) is distributed to 0.5 ml microfuge tubes and the volume adjusted to 50 ul by adding a reaction mixture comprising 0.2 mM dNTPs (dATP, dCTP dGTP, dTTP), 0.25 ug of each positive and negative oligonucleotide primer, 1 unit of TaqI polymerase, TaqI 10× buffer (5 ul), 1 mM MgCl2 (final concentration), and sterile distilled water to achieve the total volume. The TaqI polymerase is added to the reaction mixture just before use and is gently mixed, not vortexed. A layer of mineral oil, approximately 2 drops, is added to each tube and then the tubes are placed in the thermal cycler. Thirty to thirty-five cycles are general sufficient for bacterial DNA amplification. One cycle consists of 1 minute at 95° C., 1 minute at 37° C., and 1 minute at 72° C. The first cycle includes a 12 minute incubation at 95° C. to assure complete denaturation.

Oligonucleotides useful as primers or probes which specifically hybridize to the gene encoding the DnaK of P. gingivalis and used in DNA amplification and/or detection can be biochemically synthesized, using methods known in the art, from the nucleotide sequences disclosed in the present invention. The specificity of the oligonucleotides of P. gingivalis can be checked by a genebank database (Genbank) search for each individual sequence. In general, the oligonucleotides should be selected for low G—C content. For detection purposes, the oligonucleotides of the present invention may be end-labeled with a radioisotope. Probe sequences, internal to the two primers used for amplification of the gene sequence, may be end-labeled using T4 polynucleotide kinase and gamma $^{32}$P ATP. Twenty pmols of probe DNA in kinase buffer (50 mM Tris, pH 7.6 10 mM $MgCl_2$, 5 mM dithiothreitol, 0.1 mM spermidine-HCl, 0.1 mM EDTA, pH 8.0) is mixed with 120 uCi of gamma $^{32}$P ATP and incubated at 37° C. for 1 hour. Labeled probe is separated from unincorporated label on an 8% acrylamide gel run for 1 hour at 200 volts in Tris Borate EDTA (TBE) buffer at room temperature. Labeled probe is first located by exposing the acrylamide gel to x-ray film for three minutes. The resulting autoradiogram is then positioned under the gel, and the band containing the labeled probe was excised from the gel. The gel slice is pulverized in one milliliter of sterile distilled water, and the probe is eluted by shaker incubation overnight as 37° C. The eluted probe is separated from the gel fragments by centrifugation using a chromatography prep column. Radioactivity of the probe is determined, by counting one microliter of the labeled probe on a glass fibre filter, by liquid scintillation. Such probe sequences may be chosen from any of the sequences disclosed herein provided the probe sequence is internal to the two primers used for amplification of the desired nucleotide sequence disclosed in the present invention.

Alternative methods known in the art may be used to improve the detection of amplified target sequences in accordance with the compositions and methods of the present invention. The sensitivity of detection of the amplified DNA sequences can be improved by subjecting the sequences to liquid hybridization. Alternative methods of detection known in the art, in addition to gel electrophoresis and gel electrophoresis with Southern hybridization and autoradiography, that may be used with the compositions and methods of the present invention include: restriction enzyme digestion with gel electrophoresis: slot-blot hybridization with a labeled oligonucleotide probe: amplification with a radiolabeled oligonucleotide probe: amplification with a radiolabeled primer with gel electrophoresis. Southern hybridization and autoradiography; amplification with a radiolabeled primer with dot blot and autoradiography; amplification with oligonucleotides containing affinity tages (e.g. biotin, or one primer incorporating biotin and the other primer with a sequence specific for a DNA binding protein) followed by detection in an affinity-based assay (e.g. ELISA); and amplification with oligonucleotides containing fluorophores followed by fluorescence detection.

One embodiment of non-isotopic detection involves incorporating biotin into the oligonucleotide primers of the present invention. The 5'-amino group of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA from a clinical specimen. The detection for the presence or absence of amplified target sequences may be accomplished by capturing the amplified target sequences using an affinity matrix having avidin bound thereto, followed by incubation with an avidin conjugate containing an enzyme which can be used to visualize the complex with subsequent substrate development. Alternatively, the amplified target sequences may be immobilized by hybridization to the corresponding probes of the target sequence wherein the probes have been affixed onto a matrix. Detection may be accomplished using an avidin conjugate containing an enzyme which can be used to visualize the complex with subsequent substrate development.

Example 12

Methods for using antigenic proteins, peptides or chimeric peptides in diagnostic immunoassays.

The *P. gingivalis* antigens described herein, related peptides, oligopeptides or chimeras can be purified for use as immunogens in vaccine formulations; and as antigens for diagnostic assays or for generating *P. gingivalis*-specific antisera of therapeutic and/or diagnostic value. The antigens from *P. gingivalis* or oligopeptides or peptides or chimeras thereof, or recombinant protein, recombinant peptides, or recombinant oligopeptides produced from an expression vector system, can be purified with methods known in the art including detergent extraction, chromatography (e.g., ion exchange, affinity, immunoaffinity, or ultrafiltration and sizing columns), differential centrifugation, differential solubility, or other standard techniques for the purification of proteins.

In another illustration of this embodiment, a recombinant Ag1 or haeme receptor protein (HRP) was purified from a polyhistidine expression plasmid. To purify recombinant HRP by this method, the gene encoding HRP (FIG. 1) was cloned into a polyhistidine expression vector such as plasmid pRSETA (Invitrogen Corporation), such that upon expression several histidine residues ("polyhistidine tail") are attached to the amino terminus of the HRP. A fragment containing the gene encoding the HRP was ligated into the expression vector which had been previously restricted with an appropriate endonuclease and subsequently treated with calf intestinal phosphatase. The ligation mixture was used to electroporate *E. coli* strain BL21 (DE3) cells, and transformants were analyzed for recombinant plasmids containing the gene encoding HRP in the proper orientation with respect to the plasmid promoter. One such clone was isolated and was also shown to express the HRP when introduced into the *E. coli* host strain.

Recombinant HRP was purified as follows. A 15 ml volume of a culture of transformants containing the transformant was grown overnight in LB ampicillin broth at 37° C. The following morning, 135 ml of broth was inoculated with the overnight culture and grown for 1 hour at 37° C. Cells were removed by centrifugation at 5,000× g for 10 minutes at 4° C. The supernatant was concentrated to 10 ml by ultrafiltration through a 10 kDa cut off membrane and then mixed for 10 minutes at room temperature with 1.6 ml of a resin (e.g., ProBond™, Invitrogen) which, via nickel on the resin, binds to the polyhistidine tail of the recombinant HRP. The resin was then isolated by centrifugation. The HRP was eluted from the resin by first washing the resin twice with 4 ml of denaturing wash buffer (8 M urea, 20 mM sodium phosphate, 500 mM sodium chloride, pH 7.8). The resin was then washed 2 times with 4 ml volumes of denaturing wash buffer at pH 6.0. This was followed by washing the column twice with 4 ml volumes of denaturing wash buffer at pH 4.0. Fractions of 1 ml each were collected and dialyzed against phosphate-buffered saline (PBS) containing a detergent (0.1% Triton X-100). Analysis of the eluted protein by gel electrophoresis and Coomassie blue staining revealed a single band. It is estimated that this method results in a preparation of the protein which is 95% purified. The resultant purified recombinant HRP was immunoreactive with antibodies which recognize native protein.

As used throughout the specification, antigen oligopeptides are defined herein as a series of peptides corresponding to a portion of the amino acid sequence of the antigens described herein, as disclosed in the enclosed sequences that are synthesized as one or chemically-linked. Such peptides or oligopeptides can be synthesized using one of the several methods of peptide synthesis known in the art including standard solid phase peptide synthesis using terbutyloxycarbonyl amino acids (Mitchell et al., 1978, *J. Org. Chem.* 43:2845–2854), using 9-fluorenylmethyloxycarbonyl amino acids on a polyamide support (Dryland et al., 1986, *J. Chem. So. Perkin Trans. I*, 125–137); by pepscan synthesis (Geysen et al., 1987, *J. Immunol. Methods* 03:259; 1984, *Proc. Natl. Acad. Sci. USA* 81:3998); by standard liquid phase peptide synthesis; or by recombinant expression vector systems.

Modification of the peptides or oligopeptides, such as by deletion and substitution of amino acids (and including extensions and additions to amino acids) and in other ways, may be made so as to not substantially detract from the immunological properties of the peptide or oligopeptide. In particular, the amino acid sequences of the antigens described herein, or peptide or oligopeptide or chimera thereof, may be altered by replacing one or more amino acids with functionally equivalent amino acids resulting in an alteration which is silent in terms of an observed difference in the physicochemical behaviour of the protein, peptide, or oligopeptide or chimera. Functionally equivalent amino acids are known in the art as amino acids which are related and/or have similar polarity or charge. Thus, an amino acid sequence which is substantially that of the amino acid sequences depicted in the Sequence Listing herein, refers to an amino acid sequence that contains substitutions with functionally equivalent amino acids without changing the primary biological function of protein, peptide, or oligopeptide or chimera.

In an illustration of production of chimeric peptides containing epitopes of the fimbrial protein (FP) and the HRP, defined regions of the respective genes can be ligated in a construct and then expressed in an expression system wherein the plasmid expression vector (pGEX2T) directs the synthesis of foreign polypeptides in E. coli as a fusion peptides with glutathione-S-transferase (GST), a 26 kilodalton protein from Schistosoma japonicum. In this mode of the embodiment, and using P. gingivalis DNA as the template, selected regions of the genes encoding FP-HRP can be amplified by the polymerase chain reaction using selected oligonucleotides. The oligonucleotides are designed so that the resulting amplified gene fragments after ligation contains a BamHI restriction site on it 5' end, and an EcoRI restriction site on the 3' end so that the amplified chimeric fragment can be directionally cloned into pGEX2T. The sequence of each recombinant plasmid is confirmed by dideoxy sequencing. To purify each recombinant peptide, the respective recombinant plasmid containing the chimeric gene fragment is transformed into E. coli JM109. The transformant is grown in 400 ml of LB broth containing 25 ug/ml of ampicillin by adding forty ml of an overnight culture to 360 ml of broth, and incubating for 1.5 hours at 37° C. with shaking. IPTG is added to 0.01 mM and the culture incubated for an additional 3 hours. Cells are centrifuged at 5000× g and the cell pellet resuspended in 5 ml of PBS. Cells are sonicated and the mixture centrifuged at 10,000× g for 10 minutes. The supernatant is mixed with 0.5 ml of preswelled glutathione-agarose beads. After mixing for 2 minutes at room temperature, the beads (with fusion peptide bound to the glutathione) are washed 2 additional times with PBS containing 1% triton-X-100. The beads are then washed once in 0.05M Tris, pH 8.0. To cleave the FP-HRP chimeric peptide form the glutathione-S-transferase, the washed beads are incubated in 0.25% (final concentration) human thrombin in Tris buffer for 1 hour at room temperature. A protease inhibitor, PMSF, is then added to a concentration of 100 ug/ml. The beads are removed by centrifugation and the supernatant contains the purified FP-HRP chimeric peptide. Immunoblot assays affirm that the fusion peptides are immunoreactive, with Ag1- and Ag2-specific rabbit polyclonal antisera.

Purified antigens, peptides, oligopeptides and chimeras may be used as antigens in immunoassays for the detection of P. gingivalis-specific antisera present in the body fluid of an individual suspected of having an infection caused by P. gingivalis. The detection of Ag(1–4) or related peptides in immunoassays, includes an immunoassay known in the art including, but not limited to, radioimmunoassay, enzyme-linked immunosorbent assay (ELISA), "sandwich" assay, precipitin reaction, agglutination assay, fluorescent immunoassay, and chemiluminescence-based immunoassay.

Example 13

Methods and compounds for formulations related to Ag(1–4) and related peptides and chimeras.

This embodiment of the present invention relates to antigens and/or peptides or oligopeptides or chimeras thereof, to be used in as immunogens in a prophylactic and/or therapeutic compositions for active immunization to protect against or treat infections caused by P. gingivalis. For vaccine purposes, an antigen of P. gingivalis comprising a bacterial protein should be immunogenic, and induce functional antibodies directed to one or more surface-exposed epitopes on intact bacteria, wherein the epitope(s) are conserved amongst strains of P. gingivalis.

In one illustration of the invention, Ag4 having the properties desirable of a vaccine antigen, the protein can be purified from P. gingivalis using the method described herein in Example 6. Mice are immunized with the purified Ag4 protein (25 ug) with adjuvant (20 ug of QS21) two times at four week intervals. Blood from the immunized mice is drawn 32 days after the last immunization and the immune sera was pooled. The pooled immune sera assayed against whole bacteria (P. gingivalis strain W50) by an enzyme linked immunosorbent assay (ELISA). For the whole cell ELISA, overnight cultures of bacteria are harvested by a swab and suspended in PBS to an absorbance of 0.1 at 600 nm. Aliquots (100 ul) of the bacterial suspension are added to the wells of a 96 well microtiter plate and dried overnight at room temperature. The plates are blocked with 100 ul of 0.1% (w/v) gelatin in PBS. This, and all remaining incubations, are for one hour at room temperature. The blocking solution is removed and 100 ul of the immune sera, diluted in PBS with 0.1% (w/v) gelatin, is added to the wells and incubated. After washing three times with PBS, the bound antibodies are detected by incubating with 100ul of alkaline phosphatase conjugated recombinant protein G (1:1500 in PBS with 0.1% (w/v) gelatin). The plates are washed and color development is facilitated by the addition of 100 ul/well of p-nitrophenyl phosphate (2 mg/ml in diethanolamine), after 30 minutes, the reaction is stopped by adding 50 ul of 3M NaOH. The absorbance is read at 492 nm using an ELISA reader. Endpoint titers are determined as the reciprocal of the dilution at which the absorbance is greater than that of the blank wells.

In further illustrating that antigens from W50 possesses properties desirable of a vaccine antigen, pooled immune sera raised to strain W50 was shown to have cross-reactivity with heterologous strains.

For vaccine development, antigen-specific amino acid sequences may be purified from a host containing a recombinant vector which expresses antigen or related peptides or chimeras. Such hosts include, but are not limited to, bacterial transformants, yeast transformants, filamentous fungal transformants, and cultured cells that have been either infected or transfected with a vector which encodes antigen amino acid sequences. Peptides or oligopeptides or chimeras corresponding to portions of the antigens may be produced form chemical or enzymatic cleavage of the antigens; or chemically synthesized using methods known in the art and with the amino acid sequence deduced from the nucleotide sequence of the genes encoding the antigens as a reference. Alternatively, peptides may be produced from a recombinant vector. The protein, peptide, or oligopeptide or chimera immunogen is included as the relevant immunogenic material in the vaccine formulation, and in therapeutically effective amounts, to induce an immune response. Many methods are known for the introduction of a vaccine formulation into the human or animal to be vaccinated. These include, but are not limited to, intradermal, intramuscular, intraperitoneal, intravenous, subcutaneous, ocular, intranasal, and oral administration. The vaccine may further comprise a physiological carrier such as a solution, a polymer or liposomes; and an adjuvant, or a combination thereof. Various adjuvants are used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant (IFA), Adjuvant 65 (containing peanut oil, mannide monooleate and aluminium monostrearate), oil emulsions, Ribi adjuvant, the pluronic polyols, polyamines, Avridine, Quil A, saponin, MPL, QS-21, and mineral gels such as aluminium salts. Other examples include oil in water emulsions such as SAF-1, SAF-0, MF59, Seppic ISA720, and other particular adjuvants such as ISCOMs and ISCOM matrix. An extensive but not exhaustive list of other examples of adjuvants are listed in Cox and Coulter 1992 [In: Wong W K (ed.) *Animals parasite control utilising technology*. Bocca Raton; CRC press, 1992; 49–112]. In addition to the adjuvant the vaccine may include conventional pharmaceutically acceptable carriers, excipients, fillers, buffers or diluents as appropriate. One or more doses of the vaccine containing adjuvant may be administered prophylactically to prevent periodontitis or therapeutically to treat already present periodontitis.

Another embodiment of this mode of the invention involves the production of antigen-specific amino acid sequences as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such a antigen-specific hapten linked to a carrier molecule may be the immunogen in a vaccine formulation.

Another mode of this embodiment provides for either a live recombinant viral vaccine, recombinant bacterial vaccine, recombinant attenuated bacterial vaccine, or an inactivated recombinant viral vaccine which is used to protect against infections caused by *P. gingivalis*. Vaccina virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens such as Ag(1–4) protein, related peptides or chimeras, thereby providing long lasting immunity.

Other live vaccine vectors include: adenovirus, cytomegalovirus, and preferably the poxviruses such as vaccinia (Paoletti and Panicali, U.S. Pat. No. 4,603,112) and attenuated Salmonella strains (Stocker et al., U.S. Pat. Nos. 5,210,035; 4,837,151; and 4,735,801: and Curtiss et al., 1988, Vaccine 6:155–160). Live vaccines are particularly advantageous because they continually stimulate the immune system which can confer substantially long-lasting immunity. When the immune response is protective against subsequent *P. gingivalis* infection, the live vaccine itself may be used in a preventive vaccine against *P. gingivalis*. In particular, the live vaccine can be based on a bacterium that is a commensal inhabitant of the oral cavity. This bacterium can be transformed with a vector carrying a recombinant Ag(1–4), peptides, oligopeptides or chimeric peptides and then used to colonise the oral cavity, in particular the oral mucosa. Once colonised the oral mucosa, the expression of the recombinant protein, peptide or chimera will stimulate the mucosal associated lymphoid tissue to produce neutralising antibodies.

To further illustrate this mode of the embodiment, using molecular biological techniques such as those illustrated in Example 12, the genes encoding Ag(1–4) or gene fragments encoding one or more peptides or chimeras may be inserted into the vaccinia virus genomic DNA at a site which allows for expression of epitopes but does not negatively affect the growth or replication of the vaccinia virus vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen and without substantially affecting the immunogenicity of the expressed immunogen. A mixture of inactivated viruses which express different epitopes may be used in the formulation of a multivalent inactivated vaccine. In either case, the inactivated recombinant vaccine or mixture of inactivated viruses may be formulated with a suitable adjuvant in order to enhance the immunological response to the vaccine antigens.

In another variation of this embodiment, genetic material is used directly as the vaccine formulation. Nucleic acid (DNA or RNA) containing sequences encoding Ag(1–4), related peptides or oligopeptides or chimeras, operatively linked to one or more regulatory elements can be introduced directly to vaccinate the individual ("direct gene transfer") against pathogenic strains of *P. gingivalis*. Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid: cationic liposome complex [Zhu et al., 1993, *Science* 261:209–211]. Other effective methods for delivering vector DNA into a target cell are known in the art. In one example, purified recombinant plasmid DNA containing viral genes has been used to inoculate (whether parentally, mucosally, or via gene-gun immunization) vaccines to induce a protective immune response (Fynan et al., 1993, *Proc. Natl. Acad. Sci. USA* 90:11478–11482). In another example, cells removed from an individual can be transfected or electroporated by standard procedures known in the art, resulting in the introduction of the recombinant vector DNA into the target cell. Cells containing the recombinant vector DNA may then be selected for using methods known in the art such as via a selection marker expressed in the vector, and the selected cells may then be re-introduced into the individual to express the antigenic protein, related peptides or oligopeptides or chimeras.

One preferred method of vaccination with genetic material comprises the step of administering to the individual the nucleic acid molecule that comprises a nucleic acid sequence that encodes for one or more of Ag(1–4), related peptides, or oligopeptides or chimeras, wherein the nucleic acid molecule is operatively linked to one or more regulatory sequences necessary for expression. The nucleic acid molecule can be administered directly, or first introduced into a viral vector and administered via the vector. The nucleic acid molecule can be administered in a pharmaceutically acceptable carrier or diluent and may contain compounds that can enhance the effectiveness of the vaccine. These additional compounds include, but are not limited to, adjuvants that enhance the immune response, and compounds that are directed to modulate the immune response, e.g. cytokines, collectively referred to as "immune modulators"; or other compounds which increase the uptake of nucleic acid by the cells, referred to as "nucleic acid uptake enhancers". The immunization with the nucleic acid molecule can be through any parental route (intravenous, intraperitoneal, intradermal, subcutaneous, or intramuscular), or via contact with mucosal surfaces of the nasopharynx, trachea, or gastrointestinal tract.

As an alternative to active immunization, immunization may be passive, i.e. immunization comprising administration of purified immunoglobulin containing antibody against Ag(1–4) epitopes.

Example 14

The following is an example of a proposed toothpaste formulation containing anti-Ag-1 antibodies.

| Ingredient | w/w |
|---|---|
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Goat serum containing anti-Ag1 | 0.2 |
| Water | balance |

Example 15

The following is an example of a proposed toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine serum containing anti-Ag2 | 0.2 |
| Water | balance |

Example 16

The following is an example of a proposed toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine milk Ig containing anti-Ag1 | 0.1 |
| Water | balance |

Example 17

The following is an example of a proposed toothpaste formulation.

| Ingredient | % w/w |
|---|---|
| Sorbitol | 22.0 |
| Irish moss | 1.0 |
| Sodium Hydroxide (50%) | 1.0 |
| Gantrez | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| anti-Ag1 mouse monoclonal | 0.3 |
| sodium lauryl sulphate | 2.00 |

Example 18

The following is an example of a proposed liquid toothpaste formulation.

| Ingredient | % w/w |
|---|---|
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| Equine Ig containing anti-Ag2 | 0.2 |
| Linolic acid | 0.05 |
| Water | balance |

Example 19

The following is an example of a proposed mouthwash formulation.

| Ingredient | % w/w |
|---|---|
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Rabbit Ig containing anti-Ag1 | 0.2 |
| Water | balance |

Example 20

The following is an example of a proposed mouthwash formulation.

| Ingredient | % w/w |
|---|---|
| Gantrez S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Mouse anti-Ag2 monoclonal | 0.3 |
| Water | balance |

Example 21

The following is an example of a proposed lozenge formulation.

| Ingredient | % w/w |
|---|---|
| Sugar | 75–80 |
| Corn syrup | 1–20 |
| Flavour oil | 1–2 |
| NaF | 0.01–0.05 |
| Mouse anti-Ag1 monoclonal | 0.3 |
| Mg stearate | 1–5 |
| Water | balance |

Example 22

The following is an example of a proposed gingival massage cream formulation.

| Ingredient | % w/w |
|---|---|
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorohexidine gluconate | 0.1 |
| Mouse anti-Ag2 monoclonal | 0.3 |
| Water | balance |

Example 23

The following is an example of a proposed chewing gum formulation.

| Ingredient | % w/w |
|---|---|
| Gum base | 30.0 |
| Calcium carbonate | 2.0 |
| Crystalline sorbitol | 53.0 |
| Glycerine | 0.5 |
| Flavour oil | 0.1 |
| Mouse anti-Ag1 and anti-Ag2 monoclonals | 0.3 |
| Water | balance |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A composition for use in raising an immune response directed against *Porphyromonas gingivalis,* the composition comprising a suitable adjuvant and/or acceptable carrier and one substantially purified *P. gingivalis* immunogen which is Antigen 1, in which Antigen 1 is an antigen of *P. gingivalis* and comprises or consists of amino acid sequence: DLENKGEATLLVTFGSSSYKAPRETYAKIEKTFAAAYPDQR (SEQ ID NO:1).

2. A composition as claimed in claim 1 in which the composition further comprises at least one additional purified *P. gingivalis* immunogen, the immunogen being selected from the group consisting of Antigen 2, Antigen 3, and Antigen 4, in which:
   Antigen 2 is an antigen of *P. gingivalis* and comprises or consists of amino acid sequence: DNPDENPLEGDITQTHTEKYVLAED (SEQ ID NO:2);
   Antigen 3 is an antigen of *P. gingivalis* and comprises or consists of amino acid sequence: DVLLLDVTPLSLGIETMGGVMTYLIDANTTIPKLK (SEQ ID NO:3); and
   Antigen 4 is an antigen of *P. gingivalis* and has an N-terminal amino acid sequence: VYNASISAVGNTSAIDPVVQIIHHN (SEQ ID NO:4).

3. A composition as claimed in claim 1 in which Antigen 1 has an amino acid sequence as shown in FIG. 1 (SEQ ID NO:6).

4. A substantially purified *P. gingivalis* antigen wherein said antigen comprises or consists of amino acid sequence: DLENKGEATLLVTFGSSSYKAPRETYAK-IEKTFAAAYPDQR (SEQ ID NO:1).

5. A substantially purified *P. gingivalis* antigen as claimed in claim 4 in which the antigen has an amino acid sequence as shown in FIG. 1 (SEQ ID NO:6).

6. An isolated DNA molecule encoding the amino acid seuence shown in FIG. 1 (SEQ ID NO:6) and in which the DNA molecule has the sequence shown in FIG. 1 (SEQ ID NO:5).

7. A recombinant host cell, the host cell being transformed with a DNA sequence having the sequence shown in FIG. 1 (SEQ ID NO:5).

8. A recombinant host cell as claimed in claim 7 in which the host cell is an oral commensal.

* * * * *

SEQUENCE LISTING

```
<160> NUMBER OF SEQ ID NOS: 15

<210> SEQ ID NO 1
<211> LENGTH: 40
<212> TYPE: PRT
<213> ORGANISM: Porphyromonas gingivalis

<400> SEQUENCE: 1

Asp Leu Glu Asn Lys Gly Glu Ala Thr Leu Leu Val Thr Phe Gly Ser
 1               5                  10                  15

Ser Tyr Lys Ala Pro Arg Glu Thr Tyr Ala Lys Ile Glu Lys Thr Phe
                20                  25                  30

Ala Ala Ala Tyr Pro Asp Gln Arg
            35                  40

<210> SEQ ID NO 2
<211> LENGTH: 25
<212> TYPE: PRT
<213> ORGANISM: Porphyromonas gingivalis

<400> SEQUENCE: 2

Asp Asn Pro Asp Glu Asn Pro Leu Glu Gly Asp Ile Thr Gln Thr His
 1               5                  10                  15

Thr Glu Lys Tyr Val Leu Ala Glu Asp
                20                  25

<210> SEQ ID NO 3
<211> LENGTH: 35
<212> TYPE: PRT
<213> ORGANISM: Porphyromonas gingivalis

<400> SEQUENCE: 3
```

Asp Val Leu Leu Leu Asp Val Thr Pro Leu Ser Leu Gly Ile Glu Thr
 1               5                  10                  15

Met Gly Gly Val Met Thr Tyr Leu Ile Asp Ala Asn Thr Thr Ile Pro
            20                  25                  30

Lys Leu Lys
        35

<210> SEQ ID NO 4
<211> LENGTH: 25
<212> TYPE: PRT
<213> ORGANISM: Porphyromonas gingivalis

<400> SEQUENCE: 4

Val Tyr Asn Ala Ser Ile Ser Ala Val Gly Asn Thr Ser Ala Ile Asp
 1               5                  10                  15

Pro Val Val Gln Ile Ile His His Asn
            20                  25

<210> SEQ ID NO 5
<211> LENGTH: 1140
<212> TYPE: DNA
<213> ORGANISM: Porphyromonas gingivalis

<400> SEQUENCE: 5
ttgcgactcg ccacatcgca tcgtttcgct catttccgcc acatcatcct ggatggaacg      60
ctcggtatag acaaccgttt gactacgtgg atgatcgtcc tatgggtgtc aattatgcta     120
ccgtaacgcc gggacgtact ttctttgctc aaatagcgat tcgattcaac aactaatgtc     180
tcacaaatta atttaagaac agagatgaaa aaactgattt tagcgacttt gggacttatg     240
gccattgcca tgctctcatg ttcaagcaac aacaaggatt tggagaacaa aggggaggct     300
actcttttgg taacgtttgg tagctcctat aaagctccac gcgaaaccta tgcgaagatt     360
gagaagactt tgccgcagc ttatcccgat caaaggataa gctggacata cacgtcttct     420
attatccgaa agaaactggc tcagcagggt atttatatcg atgctccgga tgaggctttg     480
gagaaattgg ctcgtctggg ttataagaag atcaatgtac agagtcttca tgtgattccc     540
ggccgagaat atgatgagat gatcgacttt gtcaataagt ttaaggcagc acatagtgat     600
attactgtga aggtagggcg tccgcttttc gataccgatg aagatatgcg cgaggtggca     660
gagatcttgc acaagcgttt tcagcaaacg atagagaaag gtgaagctat tgtattcatg     720
ggacacggca ccgagcatgc tgccaatgac aggtatgccc gtatcaataa gatcatgaag     780
aactatagca agttcatgat cgtcggaacc gtcgagtccg atccctctat caatgatgtt     840
attgccgaac tgaaagaaac cggtgccacg gccgtaacaa tgatgccgct gatgagtgtg     900
gcaggcgacc atgctacgaa tgatatggcc ggagatgagg acgatagctg aaagacgttg     960
ctgaccaatg ccggctacac agtttctata gacaagctgg acaatggcaa tttctcagct    1020
cttggagata tagaagagat ccggaatatc tggctcaagc atatgaaagc cacctctgct    1080
cgctaaggac gggcggatat gcaatgagac aatcaagcaa ttaagttacg agagcactta    1140

<210> SEQ ID NO 6
<211> LENGTH: 293
<212> TYPE: PRT
<213> ORGANISM: Porphyromonas gingivalis

<400> SEQUENCE: 6

Met Lys Lys Leu Ile Leu Ala Thr Leu Gly Leu Met Ala Ile Ala Met

```
         1               5                  10                 15
Leu Ser Cys Ser Ser Asn Asn Lys Asp Leu Glu Asn Lys Gly Glu Ala
             20                 25                 30
Thr Leu Leu Val Thr Phe Gly Ser Ser Tyr Lys Ala Pro Arg Glu Thr
         35                 40                 45
Tyr Ala Lys Ile Glu Lys Thr Phe Ala Ala Tyr Pro Asp Gln Arg
     50                 55                 60
Ile Ser Trp Thr Tyr Thr Ser Ser Ile Ile Arg Lys Lys Leu Ala Gln
 65                 70                 75                 80
Gln Gly Ile Tyr Ile Asp Ala Pro Asp Glu Ala Leu Glu Lys Leu Ala
                 85                 90                 95
Arg Leu Gly Tyr Lys Lys Ile Asn Val Gln Ser Leu His Val Ile Pro
            100                105                110
Gly Arg Glu Tyr Asp Glu Met Ile Asp Phe Val Asn Lys Phe Lys Ala
            115                120                125
Ala His Ser Asp Ile Thr Val Lys Val Gly Arg Pro Leu Phe Asp Thr
    130                135                140
Asp Glu Asp Met Arg Glu Val Ala Glu Ile Leu His Lys Arg Phe Gln
145                150                155                160
Gln Thr Ile Glu Lys Gly Glu Ala Ile Val Phe Met Gly His Gly Thr
                165                170                175
Glu His Ala Ala Asn Asp Arg Tyr Ala Arg Ile Asn Lys Ile Met Lys
            180                185                190
Asn Tyr Ser Lys Phe Met Ile Val Gly Thr Val Glu Ser Asp Pro Ser
            195                200                205
Ile Asn Asp Val Ile Ala Glu Leu Lys Glu Thr Gly Ala Thr Ala Val
    210                215                220
Thr Met Met Pro Leu Met Ser Val Ala Gly Asp His Ala Thr Asn Asp
225                230                235                240
Met Ala Gly Asp Glu Asp Asp Ser Trp Lys Thr Leu Leu Thr Asn Ala
                245                250                255
Gly Tyr Thr Val Ser Ile Asp Lys Leu Asp Asn Gly Asn Phe Ser Ala
            260                265                270
Leu Gly Asp Ile Glu Glu Ile Arg Asn Ile Trp Leu Lys His Met Lys
            275                280                285
Ala Thr Ser Ala Arg
            290

<210> SEQ ID NO 7
<211> LENGTH: 25
<212> TYPE: PRT
<213> ORGANISM: Dichelobacter nodosus

<400> SEQUENCE: 7

Lys Gly Pro Asp Ala Asn Pro Ala Ser Gly Val Val Gly Asn Lys Asp
 1               5                  10                 15

Thr Gly Lys Tyr Val Leu Ala Glu Ile
            20                 25

<210> SEQ ID NO 8
<211> LENGTH: 6
<212> TYPE: PRT
<213> ORGANISM: Porphyromonas gingivalis

<400> SEQUENCE: 8

Lys Tyr Val Leu Ala Glu
```

```
<210> SEQ ID NO 9
<211> LENGTH: 21
<212> TYPE: DNA
<213> ORGANISM: Porphyromonas gingivalis

<400> SEQUENCE: 9
caagcaacaa caaggatttg c                                              21

<210> SEQ ID NO 10
<211> LENGTH: 18
<212> TYPE: DNA
<213> ORGANISM: Porphyromonas gingivalis

<400> SEQUENCE: 10
ttgcatatcc gcccgtcc                                                  18

<210> SEQ ID NO 11
<211> LENGTH: 218
<212> TYPE: DNA
<213> ORGANISM: Artificial Sequence
<220> FEATURE:
<223> OTHER INFORMATION: Description of Artificial Sequence: Vector and
      sequence from Porphromonas gingivalis

<400> SEQUENCE: 11
gctcccggca tccgcttaca gacaagctgt gacgtctccg ggagctgcat gtgtcagagg    60
ttttcaccgt caccgaaacg cgcgaggctg atcgtcagtc agtcacgatg cggccgttcg   120
agtcgactct agaggatccc ccaagcaaca acaaggattt ggagaacaaa ggggaggcta   180
ctcttttggt aacgtttggt agctcctata aagctcca                           218

<210> SEQ ID NO 12
<211> LENGTH: 210
<212> TYPE: DNA
<213> ORGANISM: Artificial Sequence
<220> FEATURE:
<223> OTHER INFORMATION: Description of Artificial Sequence: Vector and
      sequence from Porphromonas gingivalis

<400> SEQUENCE: 12
gatgtgtcaa agatatctgt tcgacctgtt accgttaaag agtcgagaac ctctatatct    60
tctctaggcc ttatagaccg agttcgtata ctttcggtgg agacgagcga ttcctgcccg   120
cctatacgtt cccatggctc gagcttaagg acccctaggt gcgcttggtc taggctaaaa   180
cctcctacca gcggtggtgg tttgcacgaa                                    210

<210> SEQ ID NO 13
<211> LENGTH: 16
<212> TYPE: PRT
<213> ORGANISM: Porphyromonas gingivalis

<400> SEQUENCE: 13

Cys Ile Arg Asn Ile Trp Leu Lys His Met Lys Ala Thr Ser Ala Arg
  1               5                  10                  15

<210> SEQ ID NO 14
<211> LENGTH: 7
<212> TYPE: PRT
<213> ORGANISM: Porphyromonas gingivalis

<400> SEQUENCE: 14
```

```
Gly Ile Glu Thr Met Gly Gly
  1               5

<210> SEQ ID NO 15
<211> LENGTH: 26
<212> TYPE: PRT
<213> ORGANISM: Porphyromonas gingivalis

<400> SEQUENCE: 15

Asp Asn Pro Asp Glu Asn Pro Leu Glu Gly Asp Ile Thr Gln Thr His
  1               5                  10                  15

Thr Glu Lys Tyr Val Leu Ala Glu Asp Cys
             20                  25
```